United States Patent
Greenberger

Patent Number: 6,028,942
Date of Patent: *Feb. 22, 2000

[54] STETHOSCOPE WITH REDUCED SUSCEPTIBILITY TO INTERFERENCE FROM AMBIENT NOISE

[76] Inventor: Hal P. Greenberger, 182 Laurelwood Dr., Hopedale, Mass. 01747

[*] Notice: This patent issued on a continued prosecution application filed under 37 CFR 1.53(d), and is subject to the twenty year patent term provisions of 35 U.S.C. 154(a)(2).

[21] Appl. No.: 08/802,731

[22] Filed: Feb. 20, 1997

[51] Int. Cl.⁷ .......................................................... A61B 7/04
[52] U.S. Cl. .............................. 381/67; 181/131; 181/137
[58] Field of Search ............................... 381/67, 184, 186, 381/357; 181/126, 131–132, 137; 600/528, 586; D24/134

[56] References Cited

U.S. PATENT DOCUMENTS

| | | | |
|---|---|---|---|
| 3,989,895 | 11/1976 | O'Daniel, Sr. | 381/67 |
| 4,071,694 | 1/1978 | Pfeiffer | 381/67 |
| 4,072,822 | 2/1978 | Yamada | 381/67 |
| 4,270,627 | 6/1981 | Hill | 181/131 |
| 4,362,164 | 12/1982 | Little et al. | 600/528 |
| 4,387,784 | 6/1983 | Hill | 181/131 |
| 4,502,562 | 3/1985 | Nelson | 181/131 |
| 4,903,794 | 2/1990 | Klippert et al. | 181/131 |
| 5,492,129 | 2/1996 | Greenberger | 181/131 |
| 5,616,890 | 4/1997 | Boussignac | 181/131 |
| 5,737,429 | 4/1998 | Lee | 381/67 |

Primary Examiner—Vivian Chang
Assistant Examiner—Xu Mei
Attorney, Agent, or Firm—Brian M. Dingman

[57] ABSTRACT

A stethoscope, and a stethoscope chestpiece, with an increased signal to noise ratio. The invention concerns mechanical improvements to both traditional mechano-acoustic stethoscopes, and to electronic stethoscopes. The stethoscope chestpieces of this invention are constructed so that the transducers are responsive to the pressure differences between air pressure variations in the chestpiece air cavity which is coupled to the skin, and the air pressure variation due to ambient noise present in the environment. The result is a transducer output with increased signal to noise ratio.

43 Claims, 15 Drawing Sheets

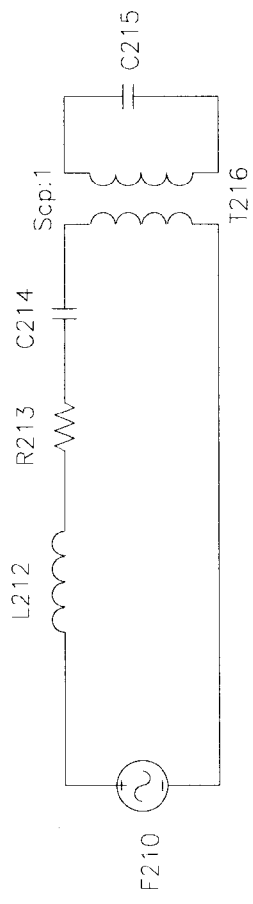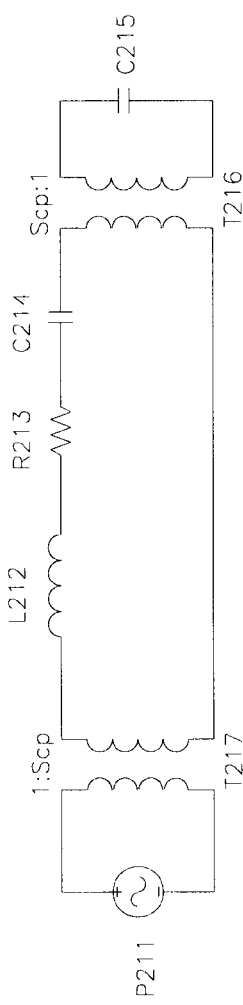

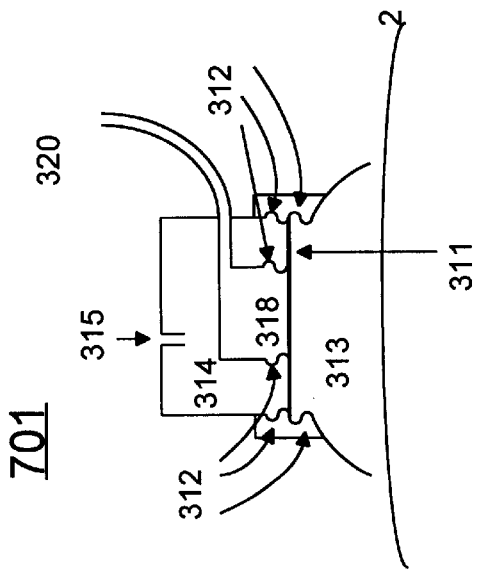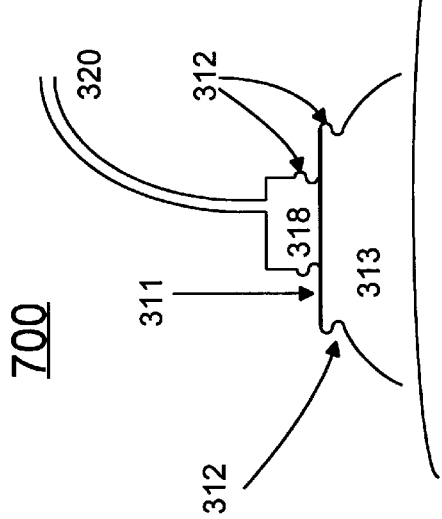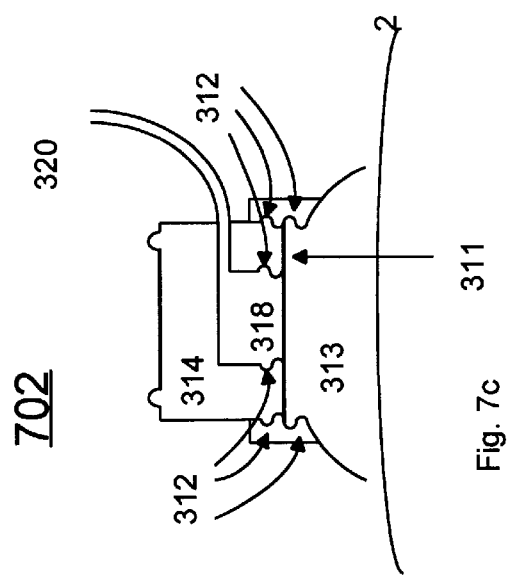

604

605

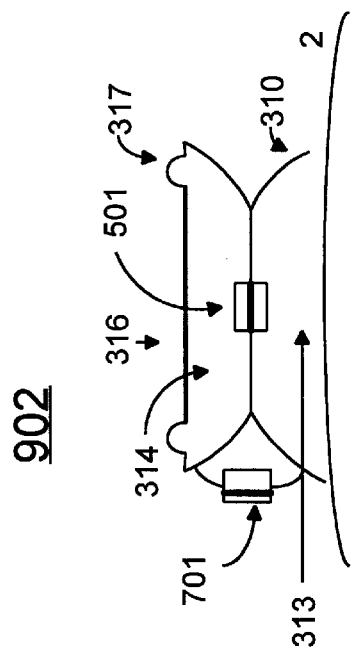
Fig. 9a
Fig. 9b
Fig. 9c

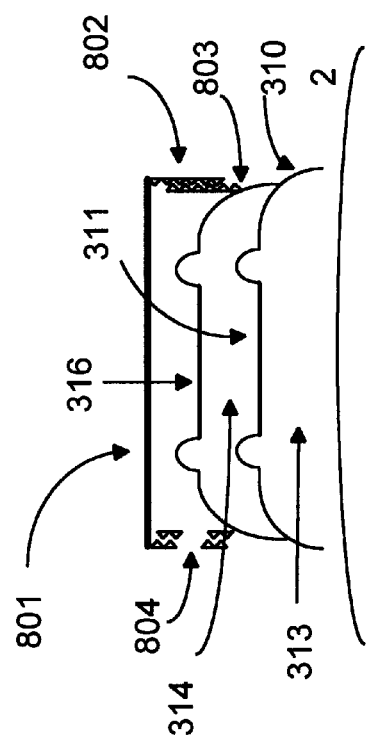

STETHOSCOPE WITH REDUCED SUSCEPTIBILITY TO INTERFERENCE FROM AMBIENT NOISE

FIELD OF THE INVENTION

This invention relates to the fields of noise reduction, and in particular relates to the use of a stethoscope in the presence of ambient noise. The invention is concerned with reducing the signal components of the output of a stethoscope chestpiece due to ambient noise, without affecting the signal components of the chestpiece output signal due to the internal physiologic processes of a patient, when the stethoscope chestpiece is placed against the patient's body.

DESCRIPTION OF PRIOR ART

Traditional passive mechano-acoustic stethoscopes employ a chestpiece, which is designed to transduce the vibrations of a patient's chest wall (or other portions of the body that may be of interest) into air pressure variations. These air pressure variations are then conducted through tubes to ear pieces that fit into the user's ear canals. The chestpiece is able to convert the skin vibrations into air pressure variations by coupling a small air cavity to the skin. This is commonly done using both bell and diaphragm type chestpieces. In the diaphragm type chestpiece, the diaphragm seals an air cavity, which is located behind the diaphragm, from the outside environment. The user places the chestpiece on the patient so that the diaphragm is in contact with the patient's skin. In the bell type chestpiece, the air cavity of the bell is sealed from the outside environment when the bell is placed against the skin. In the bell type chestpiece, the skin acts as the diaphragm. For both chestpiece types, when the skin vibrates, it causes the volume of air in the air cavity to change in sympathy with the skin vibration This in turn causes the air pressure inside the air cavity to vary in sympathy with the skin vibration. These air pressure variations are then conducted through tubes to the user's ears.

Electronic stethoscopes that use microphones as transducers employ an air cavity in the same manner as described above for passive chestpieces. Skin vibrations relative to the chestpiece body are transduced into air pressure variations within the air cavity. A microphone is coupled to the air cavity to transduce the air pressure variations into an electrical signal. Microphones used for this purpose are typically pressure responding devices.

When ambient noise is present within the environment, it will cause the skin of the patient to vibrate. The stethoscope chestpiece will transduce this vibration along with the desired vibration due to internal physiologic processes. In a mechano-acoustic stethoscope, the pressure signal conducted to the user's ears will be a combination of pressure variations in the chestpiece air cavity due to the patient's internal physiologic processes, and pressure variations due to vibration of the patient's skin caused by ambient noise. Traditional stethoscopes are not capable of distinguishing between these sources of air pressure variations. This is the primary reason why traditional stethoscopes are not useful in high noise environments.

An electronic stethoscope that uses a microphone to sense the pressure within the air cavity of the chestpiece, or other types of transducers that directly sense either the displacement, velocity, or acceleration of the patient's skin, will also be corrupted by ambient noise. Again, ambient noise causes the patients skin to vibrate. All of the above transduction methods attempt to convert the patient's skin vibration into an electrical signal, and all of them will have a component of their output that is due to internal physiologic processes and a component of their output due to ambient noise.

In the authors previous U.S. Pat. No. 5,492,129, FIGS. 10A through 10D showed different transducer configurations that had a reduced sensitivity to skin vibrations due to ambient noise, while maintaining a sensitivity to skin vibrations due to internal physiologic processes equivalent to conventional transduction methods. The fundamental principal underlying the behavior of those transducer configurations, along with some additional configurations based on the fundamental principal described, are developed in more detail in this patent disclosure.

In addition, U.S. Pat. No. 5,492,129 described methods for actively compensating for the corruption of the chestpiece output signal by airborne ambient noise sources. These methods employ two transducers, where one transducer outputs a signal due to the patient's skin vibration (which contains a component due to ambient noise and a component due to internal physiologic processes) and the second transducer was positioned so that it outputs a signal representative of only the ambient noise present in the environment. The output signal of the second transducer is then either directly subtracted, or first filtered before it is subtracted, from the output of the first transducer, so that the noise portion of the first transducer output is canceled. These methods will also be developed here for use with the new chestpiece embodiments.

Finally, mechano-acoustic stethoscope embodiments will be described, where the sensitivities of the various embodiments to internal physiologic processes are similar to existing mechano-acoustic stethoscopes, and where the sensitivities of the various embodiments to ambient noise is significantly reduced compared to existing mechano-acoustic stethoscopes.

SUMMARY OF THE INVENTION

The fundamental idea behind the new chestpiece configurations is relatively simple. The chestpiece embodiments of the invention of this disclosure are arranged so that a first chestpiece air cavity is coupled to the patient's skin. The air cavity can be directly coupled to the patient's skin as is done in bell type stethoscopes. The air cavity can also be coupled to the patient's skin through a diaphragm, where one side of the diaphragm contacts the patient and the other side is coupled to the air cavity, as is done in traditional diaphragm type stethoscopes. In either case, air pressure variation within this cavity will have a component due to internal physiologic processes and a component due to ambient noise.

The various embodiments also include some form of transducer. The transducers are designed to output a signal that is proportional to an acoustic pressure difference between two points in space. The chestpieces are constructed so that the transducers are responsive to the pressure difference between the air pressure variations in the first chestpiece air cavity, and the air pressure variation due to ambient noise present in the environment. The various embodiments couple the transducer to the ambient noise in different ways, which varies the performance and complexity of the overall system.

One method of achieving a signal that is representative of the pressure difference between two points in space is to separately measure the pressure at the two points with simple pressure responding transducers, and then subtract the output of one from the other. This is not an optimal solution. First, two transducers are required instead of one. Second, means for performing the subtraction are required. Third, individual differences in the pressure transducers will affect the degree to which the output of their subtraction matches the true differential pressure.

A second method of achieving a signal that is representative of the pressure difference between two points in space is to first separate the two points in space with a diaphragm that is free to move. The pressure difference is transformed by the diaphragm into a force difference. This force difference will cause the diaphragm to move in response. The motion of the diaphragm can then be transduced into whatever form is desired for further processing. The diaphragm motion can be transduced into an electrical signal, which can be processed as desired, and then converted back into an acoustic signal by a headset of some type for presentation to the user's ears. The processing could involve various forms of linear and non linear signal processing, and intermediate storage in some form (magnetic tape, digital conversion and storage on a computer, etc.), before being finally presented to the user. The diaphragm motion could also be directly transduced into an acoustic pressure, which could be conducted through tubes to the user's ears, as is done in traditional stethoscopes.

The chestpiece embodiments of this disclosure employ a primary diaphragm to convert a pressure difference into a force difference. The pressure applied to the first side of the primary diaphragm is due to vibration of the patient's skin (which has a component due to internal physiologic processes and a component due to ambient noise). At the same time, a pressure is also applied to the second side of the primary diaphragm, where this pressure is due only to ambient noise.

The net force applied to the primary diaphragm is proportional to the pressure difference applied to the first and second sides of the diaphragm. The vibration of the primary diaphragm is proportional to the net force applied. The primary diaphragm is located in the chestpiece assembly so that the resulting motion of the primary diaphragm will be analogous to the component of the patient's skin vibration that is due only to internal physiologic processes. The motion of the primary diaphragm is then transduced. It can be converted into an electrical signal and used in an electronic stethoscope system. There are numerous methods that can be used to convert the motion of a surface into an electrical signal. The primary diaphragm vibration can also be transduced directly into an acoustic pressure that can be conducted through tubes to the user's ears, as is done in conventional mechano-acoustic stethoscopes.

There are three basic chestpiece embodiments that will be described in detail that have value for use in both electronic and mechano-acoustic stethoscopes. These different embodiments are differentiated from each other by the method in which the second side of the primary diaphragm is coupled to the ambient noise source.

In the first embodiment, the first side of the primary diaphragm is coupled to a first chestpiece air cavity, which in turn is coupled to the patient's skin, either directly (as in a bell type stethoscope chestpiece), or through a chestpiece diaphragm (as in a traditional diaphragm type stethoscope). The second side of the primary diaphragm is directly exposed to free space.

In a second embodiment, the first side of the primary diaphragm is coupled to a first chestpiece air cavity, which in turn is coupled to the patient's skin, either directly (as in a bell type stethoscope chestpiece), or through a chestpiece diaphragm (as in a traditional diaphragm type stethoscope). A second air cavity is coupled to the second side of the primary diaphragm. This second cavity is in turn coupled to the ambient noise source through acoustic mass and acoustic resistance elements, which can be formed as a tube or tubes with finite area, finite length and arbitrary cross section.

The acoustic mass element and second air cavity form a second order low pass filter that is located in the transmission path between the second side of the primary diaphragm and the ambient noise source. The design intent is to choose the second air cavity volume and tube geometry so that the transfer function from the ambient noise source to the pressure applied to the second side of the primary diaphragm is as close a match as possible to the transfer function from the ambient noise source, through the patient's skin and chestpiece first air cavity, to the pressure applied to the first side of the primary diaphragm. It will be shown later that the transfer function from ambient noise source to the first chestpiece air cavity has a second order low pass character.

This second embodiment has additional complexity as compared to the first embodiment, but it also will have an improved ability to cancel the effects of ambient noise on the output signal of the chestpiece. However, it is not possible for this second embodiment to completely cancel the effects of ambient noise, as the topology of the elements coupled to the second side of the primary diaphragm do not exactly match the topology of the elements coupled to the first side of the primary diaphragm.

In a third embodiment, the first side of the primary diaphragm is coupled to a first chestpiece air cavity, which in turn is coupled to the patient's skin, either directly (as in a bell type stethoscope chestpiece), or through a chestpiece diaphragm (as in a traditional diaphragm type stethoscope). A second air cavity is coupled to the second side of the primary diaphragm, as was the case for the second embodiment. However, in this third embodiment the acoustic mass element is replaced by a secondary diaphragm. The first side of this secondary diaphragm is coupled to the second chestpiece air cavity. The second side of this secondary diaphragm is exposed to free air. The design intent again is to choose the second air cavity volume and secondary diaphragm mechanical properties so that the transfer function from the ambient noise source to the pressure applied to the second side of the primary diaphragm is as close a match as possible to the transfer function from the ambient noise source through the patient's skin and first chestpiece air cavity to the pressure applied to the first side of the primary diaphragm.

This third embodiment has the greatest ability to cancel the effects of ambient noise on the stethoscope chestpiece output. The electrical circuit models for this third embodiment will show that the topology of the elements coupled to the second side of the primary diaphragm match the topology of the elements coupled to the first side of the primary diaphragm. This embodiment also is slightly more complex than the second embodiment. The design and assembly of a secondary diaphragm that matches the characteristics of human skin requires greater development effort. Note that the only properties of skin that the diaphragm must emulate are its bulk mass, compliance, and damping.

It should also be noted that the characteristics of the skin will vary among patients. Different individuals have different skin characteristics. It is straightforward to design chestpieces where the primary diaphragm vibration has a reduced sensitivity to variations in the compliance of skin among individuals. In addition, the mechanical resistance of the skin does not have a great effect on the overall performance of the system. Therefore, variations in skin mechanical resistance do not need to be compensated for acceptable operation. However, variation in skin mass does have a large effect on the overall performance of the system, and it is not straightforward to design a chestpiece with reduced sensitivity to skin mass variation.

The variation in skin mass can be accommodated through the incorporation of a user adjustable mass element. The variable mass element can be tuned to compensate for variation in the skin mass among individuals. The second embodiment employs an acoustical mass element that is formed from a tube assembly. The acoustical mass of the tube can be varied by changing either the area or length of the tube (or both). The preferred method for accomplishing a variable acoustic mass is to vary the tube length. The third embodiment uses a secondary diaphragm as a mass element. The effective moving mass of a diaphragm can be varied by varying the acoustical air load applied to the diaphragm. The preferred method for accomplishing this is to vary the height of a plate assembly that is located above the side of the secondary diaphragm that is exposed to free air.

Each of the three embodiments incorporates a primary diaphragm that vibrates, where the ratio of vibration of the primary diaphragm due to internal physiologic processes compared to the vibration of the primary diaphragm due to ambient noise is much greater than the ratio of skin vibration due to internal physiologic processes compared to skin vibration due to ambient noise. The vibration of the primary diaphragm will have a much greater signal to noise ratio than the vibration of the patient's skin. The stethoscope chestpieces then transduce the vibration of the primary diaphragm with its improved signal to noise ratio. The transduced signal will then also have an improved signal to noise ratio.

There are numerous ways in which the vibration of the primary diaphragm can be transduced. The invention is not limited in the choice of transduction method used to convert the diaphragm vibration into an acoustic signal that can be heard by the user. The diaphragm displacement, velocity, or acceleration could be transduced into a form (acoustical or electrical) which can be manipulated and ultimately presented to the user's ears.

It was discussed earlier that the vibration of the primary diaphragm is proportional to the pressure difference between the front and rear of the diaphragm in the various embodiments. One transduction method for converting a pressure difference into an electrical signal that has particular appeal uses a microphone diaphragm as the primary diaphragm. Pressure gradient microphones generate an output signal that is proportional to the pressure difference between the front and rear sides of the diaphragm. This is the exact behavior that is required in the three embodiments of the current invention. The front of the pressure gradient microphone diaphragm is coupled to the first chestpiece air cavity and the rear of the pressure gradient microphone diaphragm is coupled to ambient noise in free air (either directly or through acoustical and/or mechanical filter elements).

It is also possible to transduce the vibration of the primary diaphragm directly into an acoustic pressure which can be conducted through tubes to the user's ears, as is done in traditional mechano-acoustical stethoscopes. It is possible to achieve the inherent ambient noise cancellation of the new chestpiece embodiments without the need to use electronic signal processing. The transduction into acoustic pressure is straightforward. A portion of the primary diaphragm is coupled to another air cavity. Vibration of the diaphragm causes air pressure variations in this additional cavity. These air pressure variations are then conducted through tubes to the user's ears. There are numerous ways in which a chestpiece system can be configured to accomplish this.

Finally, the new chestpiece embodiments can be used in active noise cancellation stethoscopes, such as those described in the author's previous U.S. Pat. No. 5,492,129. In the active noise cancellation stethoscopes described in U.S. Pat. No. 5,492,129, two sensors are used; one is a body sound sensor and the other is an ambient noise sensor. The chestpiece embodiments of the present invention that use a pressure gradient microphone would be used as the body sound sensor in an active noise cancellation stethoscope. A second sensor is used as the ambient noise sensor. The outputs of these sensors would then be used in a similar manner as was described in U.S. Pat. No. 5,492,129. The primary difference is that the new body sound sensors have inherently less contamination from ambient noise than previously described body sound sensors described in U.S. Pat. No. 5,492,129. When the new chestpiece embodiments are used as body sound sensors in active noise cancellation stethoscopes, the total noise cancellation achievable will be greater than when the previously described body sound sensors are used. The noise cancellation inherent in the new body sound sensors adds to the cancellation achieved by the active noise cancellation signal processing circuitry included in the active noise canceling stethoscope, to increase the total noise cancellation achieved.

OBJECTS OF THE INVENTION

It is an object of this invention to provide a stethoscope chestpiece with reduced sensitivity to ambient noise.

It is a further object of this invention to provide a stethoscope chestpiece construction method that can be applied to electronic and mechano-acoustic stethoscopes.

It is a further object of this invention to provide a stethoscope chestpiece with reduced sensitivity to ambient noise, that is compatible with active noise cancellation systems.

BRIEF DESCRIPTION OF THE DRAWINGS

Other objects, features and advantages will occur to those skilled in the art from the following description of the preferred embodiments, and the accompanying drawings, in which:

FIG. 2a is an electrical circuit model of the stethoscope of FIG. 1 when only forces generated by internal physiologic processes are considered.

FIG. 2b is an electrical circuit model of the stethoscope of FIG. 1 when only an external ambient noise source is considered.

FIG. 7a is a schematic representation of an alternative construction of the system of FIG. 6a.

FIG. 7b is a schematic representation of an alternative construction of the system of FIG. 6b.

FIG. 7c is a schematic representation of an alternative construction of the system of FIG. 6c.

FIG. 9a is a schematic representation of the first chestpiece embodiment of this invention used as a body sound sensor, with an added ambient noise sensor directly exposed to free air, for use with an active noise cancellation stethoscope.

FIG. 9b is a schematic representation of the second chestpiece embodiment of this invention used as a body sound sensor, with an added ambient noise sensor directly exposed to free air, for use with an active noise cancellation stethoscope.

FIG. 9c is a schematic representation of the third chestpiece embodiment of this invention used as a body sound sensor, with an added ambient noise sensor directly exposed to free air, for use with an active noise cancellation stethoscope.

FIG. 10 shows a representation of a user adjustable acoustic compliance element.

FIG. 11 shows a representation of a user adjustable acoustic mass element.

FIG. 12 shows an alternative representation of a user adjustable acoustic mass element.

DETAILED DESCRIPTION OF THE PREFERRED EMBODIMENTS

Figure 1:
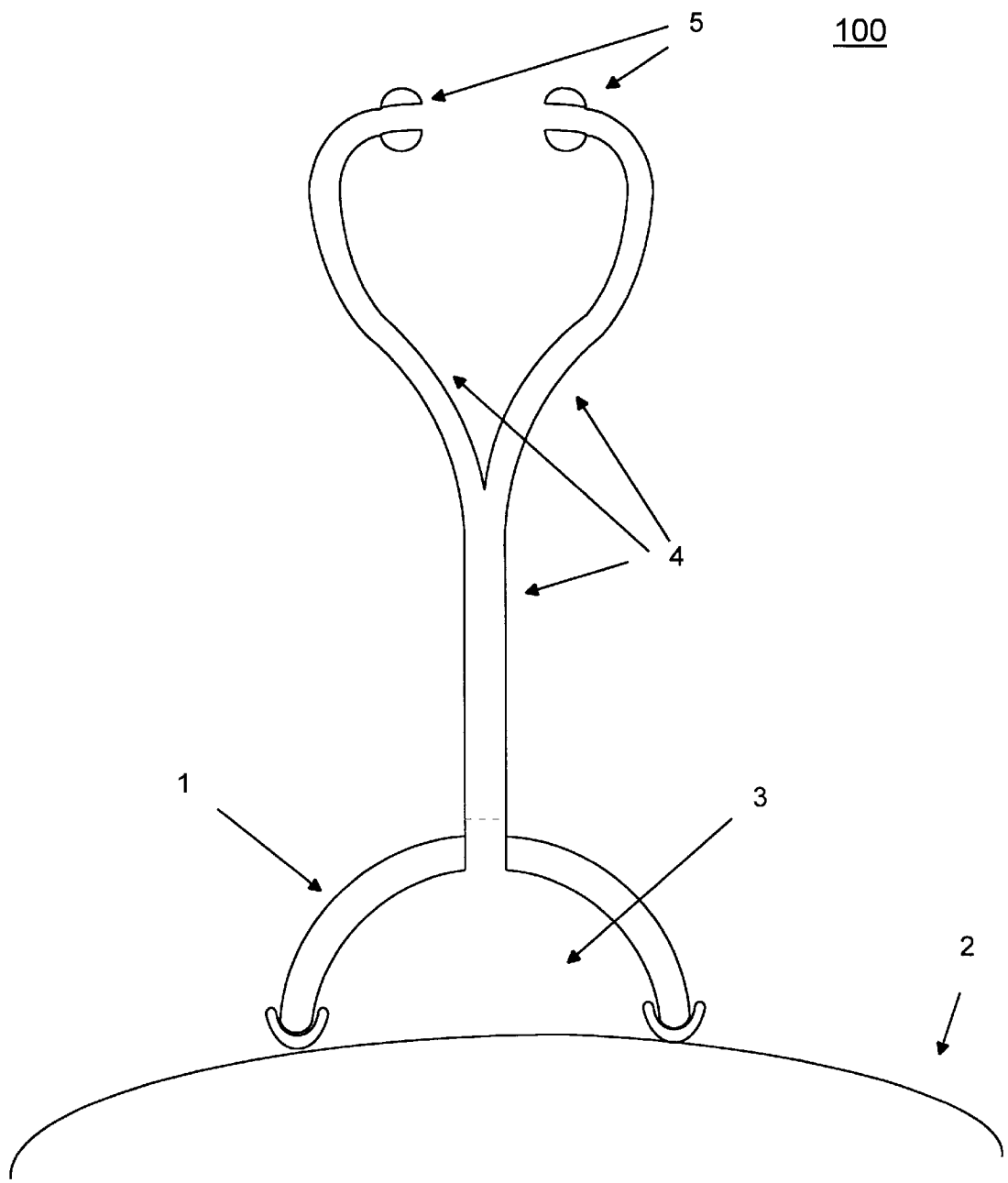
FIG. 1 is a schematic diagram of the principal components of a traditional passive mechano-acoustic stethoscope.

FIG. 1 shows a schematic representation of a traditional bell type stethoscope. Chestpiece 1 of stethoscope 100 is placed against patient's skin 2. Vibration of patient's skin 2 causes the air pressure in first chestpiece air cavity 3 of chest piece 1 to alternate in sympathy with the skin vibration. The pressure variation in cavity 3 is conducted to the user's ears through tubes 4 that connect to stethoscope ear pieces 5. It is intended that ear pieces 5 are placed in the users ears, and provide an air tight seal to the user's ear canals.

Analogous electrical circuit models for the operation of traditional stethoscope 100 are given by circuits 200 and 201 in FIGS. 2a and 2b. FIG. 2a shows the model of the traditional stethoscope when only internal physiologic forces are considered. FIG. 2b shows the model for the stethoscope when only ambient noise is considered. These models can be analyzed separately and the results combined, as the systems are linear and the principle of superposition holds.

In the electrical circuit analogy used to create the models, force and pressure are analogous to electrical voltage, and velocity and volume velocity are analogous to electrical current. This analogy is used throughout for all electrical circuit models shown. Force source 210 represents forces generated by physiologic processes occurring inside the patient's body. Pressure source 211 represents ambient noise. Inductor 212 represents the mechanical mass of the patient's skin. Resistor 213 represents the mechanical resistance of the patient's skin. Capacitor 214 represents the mechanical compliance of the patient's skin. Inductor 212, resistor 213 and capacitor 214 form a series resonant circuit model for the patient's skin. This model is an approximation to the actual mechanical impedance of the patient's skin, but it has been found to be an accurate representation in the frequency range of interest.

Capacitor 215 represents the acoustic compliance of the volume of chestpiece air cavity 3 shown in FIG. 1. Transformer 216 couples the acoustical impedance of the chestpiece air cavity to the mechanical impedance of the patient's skin. Transformer 217 couples the ambient noise source (which is an acoustic pressure source) to the mechanical impedance of the patient's skin.

The voltage across capacitor 215 is the primary variable of interest in the model. The voltage across capacitor 215 represents the air pressure developed in the chestpiece air cavity. It can easily be shown that the transfer function from ambient noise source to the air pressure within chestpiece air cavity 3 of a traditional stethoscope has a second order low pass character. It can also easily be shown that the transfer function from internal physiologic force source to the air pressure within the chestpiece air cavity 3 of a traditional stethoscope has a second order low pass character.

Figure 3B:
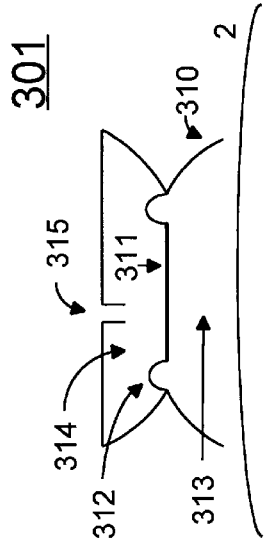
FIG. 3b is a schematic representation of the second chestpiece embodiment of this invention where the first side of the primary diaphragm is coupled to a first chestpiece air cavity and the second side of the primary diaphragm is coupled to a second air cavity, where this second air cavity is coupled to free space through an acoustic mass element.
Figure 3D:
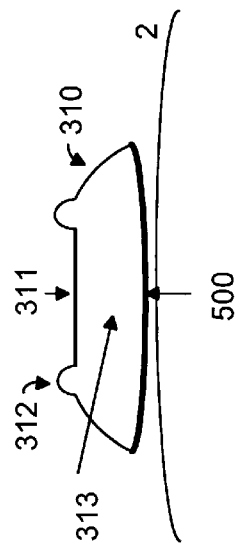
FIG. 3d is a schematic representation of the first chestpiece embodiment of this invention where the first side of the primary diaphragm is coupled to the chestpiece air cavity and the second side of the primary diaphragm is coupled to free space, and where the first chestpiece air cavity is coupled to the patient's skin through a traditional diaphragm.
Figure 3A:
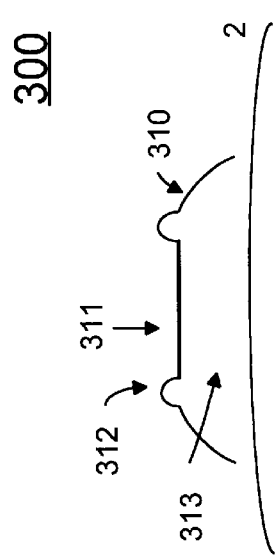
FIG. 3a is a schematic representation of the first chestpiece embodiment of this invention where the first side of the primary diaphragm is coupled to the chestpiece air cavity and the second side of the primary diaphragm is coupled to free space.

A schematic representation of a first embodiment of the current invention is shown in FIG. 3a. First chestpiece air cavity 313 is formed when chestpiece body 310 is coupled to patient's skin 2. This is the same construction used in traditional bell type stethoscope chestpieces. The front side of primary diaphragm (transducer means) 311 is exposed to first chestpiece air cavity 313, and the back side of primary diaphragm 311 is exposed to free air. Primary diaphragm means 311 is shown connected to chestpiece body 310 through compliant element 312. Compliant element 312 will also have a mechanical resistance. It should be noted that the construction of diaphragm 311 is not required to have a separate compliant element or a separate resistance element. It is possible to design a diaphragm that is made from a single material, where the material has the required mass, compliance, and resistance for optimal use in the intended application. A separate compliant element is shown for convenience only.

Primary diaphragm 311 will move when there is a net force applied. The net force is the difference between the force applied to the front of primary diaphragm 311 and the force applied to the rear of primary diaphragm 311. The displacement of primary diaphragm 311 depends on the net force applied and the mechanical impedance of the diaphragm (the mechanical mass, mechanical compliance, and mechanical resistance of the diaphragm).

The force applied to the front of primary diaphragm 311 arises from pressure variations in chestpiece air cavity 313 caused by the vibration of patient's skin 2, where:

$$f_f = P_{C1} * A_d,$$

$f_f$ is the force applied to the front of the diaphragm, $P_{C1}$ is the pressure in the chestpiece front air cavity, and $A_d$ is the area of primary diaphragm 311 coupled to first chestpiece air cavity 313. The pressure developed in first chestpiece air cavity 313 arises from vibration of the patient's skin. The vibration of the patient's skin has a component due to internal physiologic processes and a component due to ambient noise impinging on the skin. This implies that the force applied to the front of primary diaphragm 311 will have a component due to internal physiologic processes and a component due to ambient noise.

The force applied to the rear of primary diaphragm 311 is:

$$f_r = P_{211} * A_d,$$

where $f_r$ is the force applied to the rear of the diaphragm, and $P_{211}$ is the air pressure variation in free air, at the location of the rear of the primary diaphragm, due to ambient noise. Note that the rear of primary diaphragm 311 is not directly coupled to the patient's skin, so the pressure applied to the rear of primary diaphragm 311 only has a component due to ambient noise. The net pressure and net force that act on the diaphragm to cause it to move are:

$$P_{net} = P_{c1} - P_{211}$$

$$f_{net} = f_f - f_r$$

Since both $f_f$ and $f_r$ have a component due to ambient noise, and only $f_f$ has a component due to internal physiologic processes, the component of the net force due to internal physiologic processes will be the same as the component of $f_f$ due to internal physiologic processes. In addition, the component of net force due to ambient noise will be lower than the component of either $f_f$ or $f_r$ due to ambient noise. It can be seen that the net force applied to the primary diaphragm will have a greater signal to noise ratio than the pressure signal in the primary chestpiece air cavity. It follows that the vibration of primary diaphragm 311 will have a greater signal to noise ratio than the vibration of the patient's skin. This is the fundamental benefit of the current invention.

Figure 4A:
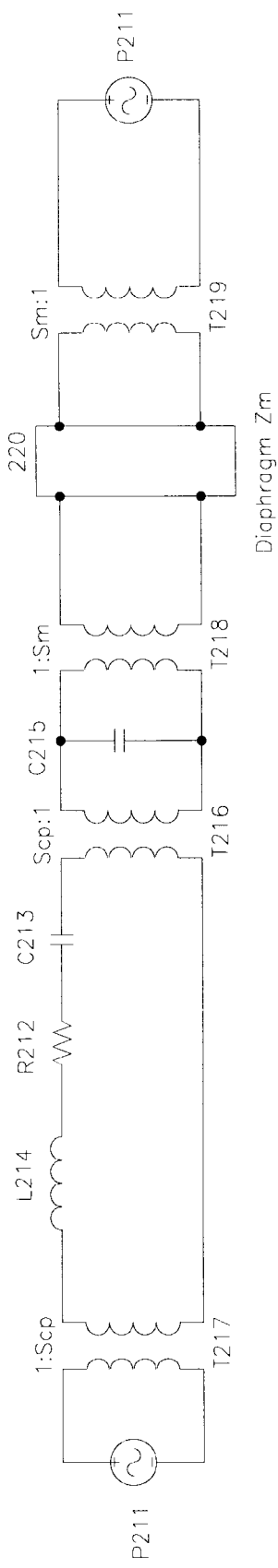
FIG. 4a is an electrical circuit model of the chestpiece of FIG. 3a, where only the response of the system to ambient noise is considered.
Figure 4B:
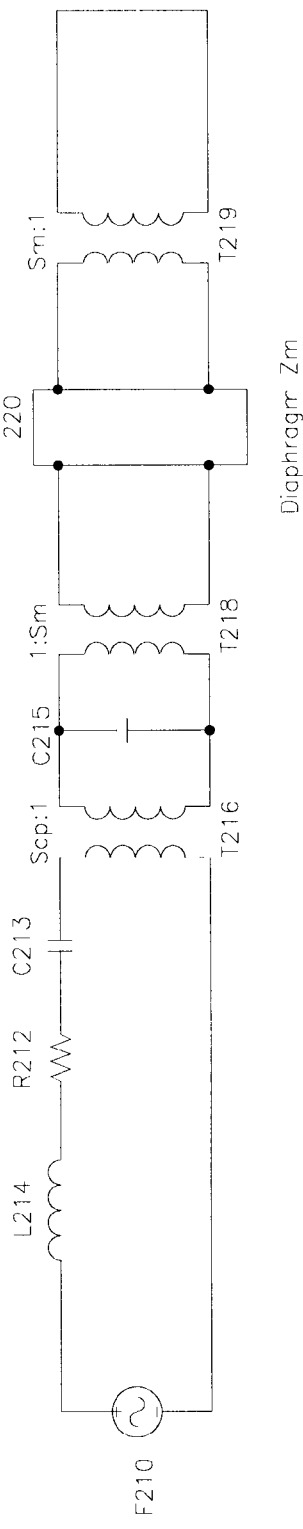
FIG. 4b is an electrical circuit model of the chestpiece of FIG. 3a, where only the response of the system to forces generated by internal physiologic processes are considered.

Circuit 400 of FIG. 4a is an electrical circuit model of the first chestpiece embodiment that is shown schematically in FIG. 3a, where only ambient noise source $P_{211}$ is considered. Circuit 401 in FIG. 4b is a model of the first chestpiece embodiment shown schematically in FIG. 3a, where only force source $F_{210}$ (which represents forces generated by internal physiologic processes) is considered. These models can be analyzed separately and the results combined, as the systems are linear and the principal of superposition holds.

It can be seen by looking at the circuit elements to the left of transformer 218 that these elements have exactly the same form as the models given in FIGS. 2a and 2b for a traditional bell type stethoscope. The voltage developed across capacitor 215 represents the acoustic pressure applied to the first side of primary diaphragm 311.

The models in FIGS. 4a and b also include some additional elements that were not present in models shown in FIGS. 2a and b for a traditional stethoscope. All of the elements that are located to the right of capacitor 215 (except for pressure source 211) in FIGS. 4a and b are new. Block 220 represents the mechanical impedance of the primary diaphragm, along with the influence, reflected into the mechanical domain, of whatever transduction method is used to transduce the primary diaphragm motion. Transformer 218 represents the coupling of the first side of the primary diaphragm to the first chestpiece air cavity. Transformer 219 represents the coupling of the second side of the primary diaphragm to free space. It can also be seen that the same ambient noise source 211 that acts on the skin is also coupled to the second side of the primary diaphragm.

It is desirable for the transfer function from internal force source to the pressure in first chestpiece air cavity 313 in FIG. 3a, which is modeled by the voltage across capacitor 215 in FIG. 4b, to match as closely as possible the second order low pass transfer function from input force to air cavity pressure of a traditional stethoscope, as was modeled in FIG. 2b. The degree to which this match is obtained depends on the nature of the mechanical impedance of primary diaphragm 311 of FIG. 3a, which is modeled by impedance block 220 in FIG. 4b. The desired behavior will be obtained if the mechanical impedance of the primary diaphragm represented by block 220 does not interact with the other circuit elements. The interaction of the mechanical impedance of primary diaphragm 311 with the other elements of the chestpiece can be minimized if the mechanical impedance of primary diaphragm 311 is made large compared to the mechanical impedance of the other system elements, over the primary frequency range of interest. (The primary frequency range of interest is from approximately 10 Hz to 1.5 Khz for traditional stethoscopes.)

If the mechanical impedance of the primary diaphragm is assumed to be infinite, then the transfer function from ambient noise to pressure applied to the front of primary diaphragm 311 will have the following form:

$$(P_f/P_{211}) = [(1/C_{215} * L_{214})]/[s^2 + (R_{212}/L_{214})*s + (C_{213} + C_{215})/(C_{213} * C_{215} * L_{214})],$$

where $P_f$ is the pressure applied to the front of primary diaphragm 311, and is the pressure within the first chestpiece air cavity 313. The transfer function from ambient noise to the pressure applied to the rear of the primary diaphragm will have the form:

$$(P_r/P_{211}) = C,$$

where $P_r$ is the pressure applied to the rear of primary diaphragm 311 and C is a constant. The net pressure applied to primary diaphragm is:

$$P_{net} = P_f - P_r$$

The transfer function from ambient noise to net pressure applied to primary diaphragm will have the form:

$$H_1(s) = (P_{net}/P_{211}) = [s^2 + (R_{212}/L_{214})*s + 1/(C_{213} * L_{214})]/[s^2 + (R_{212}/L_{214})*s + (C_{213} + C_{215})/(C_{213} * C_{215} * L_{214})],$$

which has a second order high pass shelving character, where the zeroes of the transfer function occur lower in frequency than the poles. It is interesting to look at the value of the above transfer function at zero frequency. It can be seen that for s=0, $$H_1(s) = C_{215}/(C_{213} + C_{215})$$

To minimize the net pressure due to ambient noise that acts on the primary diaphragm, at low frequencies, the compliance of the first chestpiece air cavity, modeled by capacitor 215, should be made small compared to the skin compliance, modeled by capacitor 213.

The net pressure applied to the primary diaphragm results in the net force that was described earlier, which causes the primary diaphragm to move in response. In a complete stethoscope system, the vibration of primary diaphragm 311 is then transduced into a signal that is ultimately applied to the user's ears. The primary diaphragm vibration may be transduced into an electrical signal that is subsequently transduced into an acoustic signal for presentation to the users ears, or it may be directly transduced into an acoustical signal. Transduction methods will be described in more detail later.

The above analysis assumed that the mechanical impedance of the primary diaphragm was large compared to the other mechanical impedances in the system. This assumption is necessary if it is desired to have the transfer function from internal physiologic force to first chestpiece air cavity pressure of the new embodiments match the transfer function of traditional mechano-acoustic stethoscopes from internal physiologic force to chestpiece air cavity pressure. This condition for high relative mechanical impedance of the primary diaphragm to minimize the frequency response effects on the transduction of desired body sounds holds for all of the embodiments of the current invention. It should be noted here that as long as the mechanical impedance of the primary diaphragm remains large compared to the other element impedances, all three embodiments of the current invention will have essentially the same response to internal physiologic forces as do traditional mechano-acoustic stethoscopes. This is an important point. This implies that no re-training of medical personnel will be required to use the new devices.

However, the condition of high primary diaphragm mechanical impedance is not required in order to achieve the cancellation of the effects of ambient noise. The noise reduction benefits are obtained regardless of the primary diaphragm mechanical impedance characteristics. There may be some instances where relaxing the requirement of high mechanical impedance of the primary diaphragm will be of benefit. It should be noted that the invention of this disclosure is not limited in any way with regard to the mechanical impedance of the primary diaphragm.

A high mechanical impedance can be accomplished in practice by using a primary diaphragm with high stiffness (small compliance) and low mass. This implies that the primary diaphragm should have a high resonant frequency. It is desirable for the diaphragm resonance frequency to be placed as high as practical. It is also beneficial for the primary diaphragm to have a small area. The primary diaphragm area influence is accounted for by the turns ratio of transformers 218 and 219.

In an ideal transformer, the following relationship holds:

$$Z_1 = (N_1/N_2)^2 * Z_2,$$

where $Z_1$ is the impedance reflected into the primary of the transformer, $Z_2$ is the impedance in the secondary that is reflected into the primary, and $N_1/N_2$ is the turns ratio. The turns ratio of transformer 218 is $1/S_m$, where $S_m$ is the area of the primary diaphragm. The diaphragm impedance represented by block 220, if it is reflected into the primary of transformer 218, will appear in parallel with capacitor 215. The magnitude of the diaphragm impedance when reflected into the primary will be multiplied by the square of the turns ratio. It can be seen that making the diaphragm area small will increase the turns ratio, which will further increase the magnitude of the primary diaphragm impedance with respect to the other circuit elements.

Below its resonance frequency, the primary diaphragm is stiffness controlled. That is, its motion is primarily dependent on the applied force and the stiffness of the diaphragm. The relationship between force and displacement of a spring can be stated as:

$$F = -kx,$$

where F is the force applied to the spring, k is the spring stiffness constant (which is equal to the reciprocal of the compliance), and x is displacement. It can be seen that in the frequency range of interest, if the diaphragm is operating in its stiffness controlled region, the vibration of the diaphragm will be proportional to the applied force. The implication of operation in this manner is that the component of the displacement of the primary diaphragm due to the component of applied net force due to internal physiologic processes will be directly proportional to the vibration of the patient's skin due to internal physiologic processes.

The affect of the primary diaphragm area on the system performance can be summarized as follows. The force applied to the diaphragm is proportional to the applied pressure multiplied by the diaphragm area. If the applied pressure is kept constant, as the area of the primary diaphragm is made smaller, the applied force is smaller. This implies that the displacement of the primary diaphragm will also be smaller. This further implies that as the diaphragm area is reduced, the peak volume displacement of the diaphragm is reduced (where volume displacement is area times displacement). The peak volume displacement of the first primary diaphragm becomes a smaller percentage of the first chestpiece air cavity volume as the diaphragm area is reduced. This implies the primary diaphragm has a reduced influence on the pressure variation it is designed to sense as its area is reduced.

When the primary diaphragm is operated in its stiffness controlled region, reducing the area of the primary diaphragm will reduce the interaction of the diaphragm mechanical impedance with the mechanical impedance of the other chestpiece elements. However, the area of the primary diaphragm cannot be reduced arbitrarily. Since the displacement of the primary diaphragm is proportional to the area, as the area decreases, so does the displacement. The area cannot be reduced to the point where the displacement of the primary diaphragm can no longer be accurately transduced. The extent to which the primary diaphragm area can be reduced will depend on the method used to transduce the vibration of the primary diaphragm into a useful signal. The area can be made quite small if the transduction methods used are similar to what is used in microphones. It will be discussed later than an electret pressure gradient microphone has ideal characteristics for use in all three of the fundamental embodiments of this invention.

In sum, the match of the transfer function from internal physiologic forces to net pressure applied to the primary diaphragm, for the first embodiment of this invention, to the transfer function from internal physiologic forces to pressure in the chestpiece air cavity of a traditional stethoscope, will improve as: A) the area of the primary diaphragm is reduced, B) the stiffness of the primary diaphragm is increased, and C) the mass of the primary diaphragm is decreased.

A practical system implementation has the compliance of the first chestpiece air cavity a factor of ten less than the average skin compliance, and has the primary diaphragm compliance a factor of ten smaller than the chestpiece air cavity compliance. In addition, the moving mass of the primary diaphragm should be at least a factor of ten less than the mass of the skin coupled to the chestpiece first air cavity. The area of the primary diaphragm should be reduced as much as is practical while still obtaining sufficient signal output from the transducer coupled to the primary diaphragm that transduces its vibration.

It was mentioned earlier that the transfer function from ambient noise source to the pressure in the chestpiece air cavity of a traditional bell type stethoscope had a second order low pass characteristic. It was also mentioned above that the transfer function from ambient noise source to the net pressure applied to the primary diaphragm of the first embodiment has a second order high pass shelving characteristic. This new behavior is a significant improvement. It will increase the signal to noise ratio obtained over almost the entire operating frequency range of interest. The elements of the chestpiece can be designed so that the upper corner frequency of the resulting high pass shelving frequency response occurs at the highest frequency of interest for respiration sounds. The complete output of the chestpiece can then be reduced through the addition of a low pass filter, thus further improving the complete system performance.

Figure 3C:
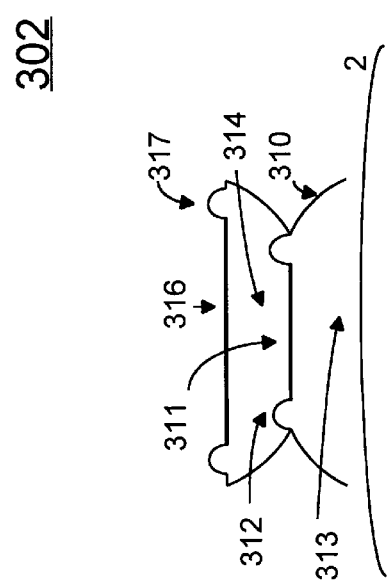
FIG. 3c is a schematic representation of the third chestpiece embodiment of this invention where the first side of the primary diaphragm is coupled to a first chestpiece air cavity and the second side of the primary diaphragm is coupled to a second air cavity, where this second air cavity is coupled to free space through a secondary diaphragm.

In the chestpiece configurations of FIGS. 3*a–c*, motion of the primary diaphragm can only occur if there is a pressure difference between the front and back sides of the diaphragm. The major improvements in body sound signal to ambient noise ratio occur when the system is configured so that the pressure on each side of the primary diaphragm due to ambient noise is as equal as possible, while vibrations due to internal physiologic processes apply pressure to only one side of the primary diaphragm. The first embodiment shown in FIG. 3*a* applies the ambient noise directly to the second side of the primary diaphragm, but ambient noise must interact with the patient's skin and the first chestpiece air cavity before it acts on the first side of the primary diaphragm.

The different characteristics of the transmission paths from ambient noise source to the first and second sides of the primary diaphragm fundamentally limit the improvement in signal to noise ratio that can be obtained. The second and third embodiments of the current invention add additional elements between the second side of the primary diaphragm and the ambient noise source in an attempt to compensate for these transmission path differences. These elements are chosen and arranged to improve the match of the transmission paths from ambient noise source to the pressure applied to the second side of the primary diaphragm, and from the ambient noise source, through the patients skin and the first chestpiece air cavity, to the pressure applied to the first side of the primary diaphragm. The improvement of the match of the transmission paths will further increase the signal to noise ratio of the primary diaphragm vibration.

Chestpiece configuration 301 in FIG. 3*b* is a schematic representation of the second embodiment of the current invention. It can be seen when chestpiece 301 is compared with chestpiece 300 in FIG. 3*a* that air cavity 314 and tube 315 have been added to the chestpiece. Air cavity 314 is coupled to the rear of primary diaphragm (transducer means) 311. Air cavity 314 is also coupled to ambient noise through tube 315. Element 315 functions primarily as an acoustical mass (but also contributes an acoustical resistance). The acoustical impedance $Z_A$ of a tube of small diameter can be written as[3]:

$$Z_A = 8\eta L/\pi a^4 + j(4/3)M_A\omega,$$

where $M_A = \rho_0 L/\pi a^2$ = acoustic mass of air in tube in kg per m$^4$ a=tube radius in m $\eta$=viscosity coefficient For air=$1.86 \times 10^{-5}$ newton-sec/m$^2$ $\omega=2\pi f$, f=frequency in Hz L=length of tube in m $\rho_o$=density of gas in kilograms per cubic m.

The above equation assumes that the diameter of the tube is small compared to the length, and the length is small compared to the wavelength of sound in the frequency range of interest. In addition to adjusting the length and diameter of the tube to obtain various values for resistance and mass, the number of holes can be varied to give additional flexibility. Tubes of round cross section are not required. Virtually any cross section can be used. However, analytic expressions for arbitrary cross sections are difficult to obtain. It should be noted that the invention is in no way limited in the cross section used, or in the number of tubes used.

The above equation for the acoustical impedance of a tube has real and imaginary terms. The real portion of the equation provides the acoustical resistance and the imaginary part gives the acoustical reactance, which in this case has the form of an acoustical mass element. Acoustical element 315 and second chestpiece air cavity 314 form a second order low pass filter that is located in the transmission path from ambient noise source to the pressure applied to the rear of primary diaphragm 311.

Figure 4C:
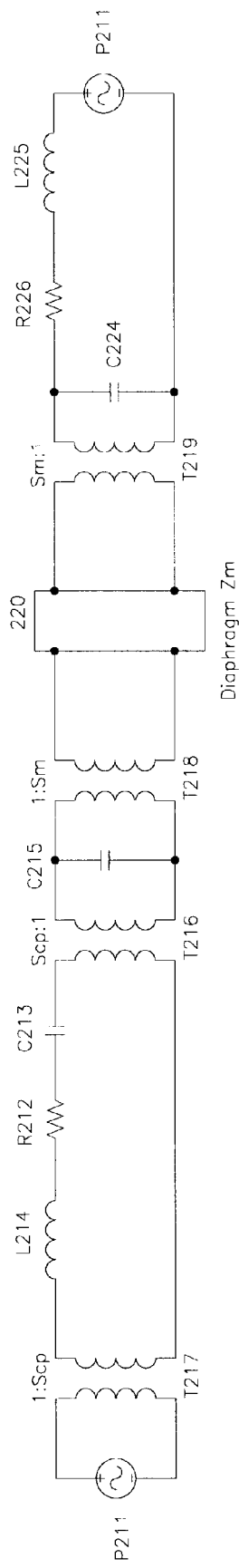
FIG. 4c is an electrical circuit model of the chestpiece of FIG. 3b, where only the response of the system to ambient noise is considered.
Figure 4D:
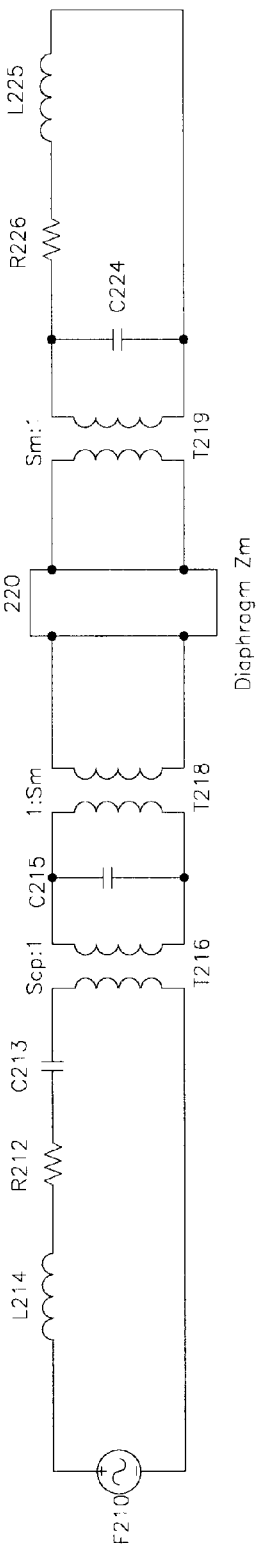
FIG. 4d is an electrical circuit model of the chestpiece of FIG. 3b, where only the response of the system to forces generated by internal physiologic processes are considered.

FIGS. 4c and d give electrical circuit models for the second embodiment chestpiece depicted in FIG. 3b. Circuit 402 of FIG. 4c is a model where only ambient noise is considered. Circuit 403 of FIG. 4d is a model where only forces due to internal physiologic processes are considered. These models can be analyzed separately and the results combined, as the systems are linear and the principal of superposition holds.

The addition of second chestpiece air cavity 314 and acoustical element 315 result in the addition of the circuit elements shown to the right of transformer 219. Capacitor 224 represents the acoustic compliance of second chestpiece air cavity 314. Inductor 225 represents the reactance portion of acoustical element 315 (which has the form of a mass element). Resistor 226 represents losses in the acoustical system. These losses are associated with air flow resistance through the structures of acoustical element 315 (given by the real term of the equation for the acoustic impedance of a small tube) and any absorption that may occur in second chestpiece air cavity 314. Transformers 218 and 219 represent the coupling of the first side of the primary diaphragm to the first chestpiece air cavity and second side of the primary diaphragm to the second chestpiece air cavity.

The left and right hand sides of the electrical circuit models in FIGS. 4c and d are a much closer match than was the case in FIGS. 4a and b, where the second side of the primary diaphragm was directly exposed to free space. The component of net pressure applied to the primary diaphragm due to ambient noise in this second embodiment will be significantly reduced compared to the first embodiment. However, it can be seen that the circuit topologies on the left and right sides of primary diaphragm mechanical impedance block 220 in FIGS. 4c and d are not an exact match. This will limit the total cancellation achievable. This limitation is addressed by the third embodiment, which is discussed in more detail shortly.

Let the transfer function from ambient noise source to pressure applied to the front of the primary diaphragm be:

$$D(s) = A/e_1(s),$$

and let the transfer function from ambient noise to the rear of the primary diaphragm be:

$$G(s) = B/e_2(s)$$

where $e_1(s)$ and $e_2(s)$ are both second order polynomials in the complex frequency variable s, and A and B are constants. The above approximations are valid if the mechanical impedance of the primary diaphragm is large compared to the other circuit elements. The transfer function from ambient noise source to net pressure applied to the primary diaphragm is then:

$$H_2(s) = D(s) - G(s) = [Ae_2(s) - Be_1(s)]/[e_1(s)e_2(s)]$$

The above transfer function has a second order numerator and a fourth order denominator. It can also be shown that the value of the above transfer function for s=0 is:

$$H_2(s) = C_{215}/(C_{213} + C_{215}),$$

which is the same result as the first embodiment. Again, it is beneficial to make the compliance of the first chestpiece air cavity small compared to the compliance of the patient's skin. The primary difference between the transfer function of the second embodiment shown above and the transfer function derived for the first embodiment is the transfer function above has an extra pair of poles. This implies that the response will roll off at higher frequencies, rather than shelve at high frequencies as the transfer function for the first embodiment does. This is a significant performance improvement over the first embodiment.

The above analysis assumed that the impedance of the primary diaphragm was large compared to the other elements of the chestpiece. The minimization of the effects of the diaphragm impedance were discussed earlier with regard to the first chestpiece embodiment, and the same discussion is also applicable here to the second chestpiece embodiment.

As was discussed above, the cancellation of the component of primary diaphragm vibration due to ambient noise is maximized when the pressures on each side of the primary diaphragm due to ambient noise are as equal as possible. The second chestpiece air cavity, and acoustical mass and resistance (that are coupled to the rear of the primary diaphragm), can be designed so that the frequency response of the low pass filter function they insert in the path between the ambient noise source and the second side of the primary diaphragm matches the frequency response of the transmission path from the ambient noise source to the first side of the primary diaphragm.

The transmission path to the first side of the diaphragm consists of the patient's skin and the first chestpiece air cavity. The second air cavity 314 and the geometry of acoustical element 315 can be chosen to match the average mechanical impedance of human skin and the compliance of the first chestpiece air cavity. However, the mechanical impedance of skin varies from individual to individual. This variation should be accounted for in the chestpiece design in order to optimize the signal to noise ratio obtained when the devices are used on different patient's.

The patient's skin is modeled in FIG. 2 (and elsewhere) as a series resonant circuit consisting of an inductor, capacitor, and resistor, which represent the mechanical mass, mechanical compliance, and mechanical resistance of the skin. All of these quantities vary among individuals. The chestpiece should be designed so that the sensitivity of the primary diaphragm vibration to variations in the mechanical impedance of the patient's skin is minimized. The chestpiece design should also include means that allow the mechanical and/or acoustical elements coupled to the rear of the primary diaphragm to be tuned by the user, to adjust for variations in skin mechanical impedance that cannot be dealt with in other ways.

In the models in FIGS. 4c and d, it can be seen that there are two compliance elements that affect the response of the ambient noise presented to the first side of the primary diaphragm; the skin mechanical compliance and the acoustic compliance of the first chestpiece air cavity, which are represented by capacitors 213 and 215 respectively. In order to minimize the effects of variation of the skin mechanical compliance on the pressure applied to the first side of the primary diaphragm, the skin mechanical compliance should be large compared to the first chestpiece air cavity equivalent mechanical compliance (which is the value of the acoustical compliance reflected into the mechanical domain). If, for example, the skin compliance were a factor of ten larger than the compliance of the first chestpiece air cavity, a 10% variation in the compliance of the skin from patient to patient would result in only a 0.9% change in total compliance of the elements that are in the signal path between the ambient noise source and the first side of the primary diaphragm.

The equivalent mechanical compliance of the first chestpiece air cavity is determined by the relationship between the volume of the air cavity and the area of the portion of the cavity that is coupled to the skin. The acoustical compliance of an air cavity and its equivalent mechanical compliance are described by the following equations:

$$C_A = V/\rho_o * c^2$$

$$C_M = 1/(S_D^2) * C_A, \text{ which gives:}$$

$$C_M = 1/(S_D^2) * [V/\rho_o * c^2]$$

where $C_A$ is the acoustical compliance, V is the volume of the air cavity, $\rho_o$ is the density of air and is approximately 1.18 kg/m$^3$, and c is the speed of sound, which is approximately 345 m/sec, $C_M$ is the equivalent mechanical compliance and $S_D$ is the area of air cavity that is coupled to the skin. It can be seen that the design variables that determine the equivalent mechanical compliance of the second chestpiece air cavity are the volume of the cavity and the area of the cavity that is coupled to the primary diaphragm.

Following the above design guideline with respect to the relative compliances of the skin and first chestpiece air cavities reduces the sensitivity of the overall system behavior to variation in skin compliance. Conforming to the above guideline will be sufficient in most circumstances to adequately account for the variability in skin compliance seen among different individuals. However, the above design criteria does not completely eliminate the effects of skin compliance variation on system behavior. The residual variation can be compensated for if the compliance of the second chestpiece air cavity is made user adjustable.

As was described earlier, the equivalent mechanical compliance of an air cavity is determined by the volume of the cavity and the area of the cavity that is coupled to another part of the system. Either of these variables could be turned into a control to achieve a user variable compliant element. The preferred embodiment for a variable compliant element is to make the volume user adjustable. It is easier to accomplish this in practice. A construction method for varying the volume of an air cavity is shown in FIG. 10. Top half of second chestpiece air cavity 314 is connected to bottom half of cavity 314 through thread assembly 800. By increasing or decreasing the number of threads that are engaged, the volume of the cavity, and as a result its acoustical compliance, can be varied.

The skin density, and therefore the mass of skin that is coupled to the first chestpiece air cavity, will vary from individual to individual. The skin mass has a direct effect on the frequency response of the ambient noise pressure that is applied to the front of the primary diaphragm. The effects of the variation of skin mass cannot easily be reduced through adjustment of the chestpiece geometry as was done above for the compliance. However, this variation in mass can be accounted for in the complete system by making acoustical element 315 user adjustable. Element 315 has an acoustical mass, and therefore an equivalent mechanical mass. The equivalent mechanical mass of element 315 can be adjusted by altering the geometry of element 315.

The acoustical mass, and the resulting equivalent mechanical mass, of acoustical element 315 can be varied by adjusting either the area of the tube or its length, or both. For a fixed area, increasing the length increases the acoustic mass. For a fixed length, decreasing the area increases the acoustical mass. Either the area or length, or both, of element 315 could be turned into a user control that can vary the acoustic mass (and the equivalent mechanical mass) contributed by element 315. The preferred method for varying the acoustic mass is to vary the length of the tube.

One method for accomplishing a variable length tube is shown in FIG. 11. The construction of FIG. 11 shows a tube within a tube. The outside diameter (OD) of inner tube 20 and the inside diameter (ID) of outer tube 30 are threaded. As inner tube 20 is unscrewed, the overall tube length increases. The length of the inner and outer tubes are chosen so that the range of acoustical mass values matches the variation of mechanical mass of skin. It should be noted that the invention is not limited in the method used to vary the acoustic mass that is coupled to the second chestpiece air cavity.

The formula for calculating the acoustical impedance of a small diameter tube was given earlier. The acoustic mass portion, and equivalent mechanical mass, of that impedance can be calculated from the following equations:

$$M_A = (4/3)(\rho_o L)/(\pi a^2), \text{ and}$$

$$M_M = S_D^2 * M_A, \text{ which can be combined into:}$$

$$M_M = S_D * (4/3)(\rho_o L),$$

where $M_A$ is the acoustical mass, $M_M$ is the equivalent mechanical mass, $\rho_o$ is the density of air, L is the length of the tube, and a is the radius of the tube, and $S_D$ is the area of the tube.

The effect of the skin mechanical resistance on the overall system behavior is less significant than the effects of skin compliance or skin mass. The mechanical resistance of the skin only affects the transfer function from ambient noise to air pressure in the first chest piece air cavity in the vicinity of the corner frequency of the transfer function. The sensitivity of the transfer function to variations in the mechanical resistance of the skin is also lower than the sensitivity of the transfer function to variation in the compliance or mass of the skin. Sufficient performance can be obtained without explicitly compensating for the variation in skin mechanical resistance among different individuals.

It is possible to perform measurements on an individual to determine a value for skin mechanical resistance. This measurement can then be made on a wide cross section of individuals and an average value can be determined. This average value will then become the design goal for the acoustical resistance of element 315. The area and length, as well as the number of tubes, for element 315, can be designed to obtain arbitrary values of acoustical resistance and acoustical mass. Additional acoustical resistance, if needed, could also be contributed by adding acoustically absorptive material to the second chestpiece air cavity.

One design procedure for designing the additional mass and compliance elements that are coupled to the second side of the primary diaphragm is to: 1) Design the equivalent mechanical compliance of the second chestpiece air cavity to match the combination of the mechanical compliance of the patient's skin with the equivalent mechanical compliance of the first chestpiece air cavity, 2) Design the equivalent mechanical mass of acoustical element 315 to match the mechanical mass of the patient's skin, and 3) Design the equivalent mechanical resistance of acoustical element 315 to match the mechanical resistance of the patient's skin.

However, the above methodology is not the only design methodology that can be used. The primary requirement is that the resonant frequency of the skin mechanical mass with the combination of the skin mechanical compliance and equivalent mechanical compliance of the first chestpiece air cavity match the resonant frequency of the acoustical compliance of the second chestpiece air cavity with the acoustical mass of acoustical element 315. This criteria is not as strict. It only requires that ratios of element values match, not all of the individual element values.

Typical values for traditional stethoscopes for the resonant frequency between skin mass and the combination of skin compliance with air cavity compliance range from 350 Hz, for large cavity bell type chestpieces, to 1000 Hz, for small cavity diaphragm type chestpieces. The resonant frequency of a representative medium sized chestpiece bell type traditional stethoscope when placed against the author's skin was measured to be 800 Hz. The acoustical compliance of the bell cavity was measured to be $1.167 \times 10^{-11}$ m$^5$/N. Assume that the second chestpiece air cavity is chosen to have the same acoustic compliance as the first chestpiece air cavity. To achieve an 800 Hz resonant frequency between the acoustic compliance of this second chestpiece air cavity with an acoustic mass, the required acoustic mass is $3.39 \times 10^3$ kg/m$^4$. The volume of the first chestpiece air cavity was measured to be 0.1 in$^3$, which will also be the volume of the second chestpiece air cavity in this example. The acoustic mass can then be realized by a small tube with a 1 cm length and a radius of 0.12 cm.

Chestpiece configuration 302 in FIG. 3c is a schematic representation of the third embodiment of the current invention. It can be seen when chestpiece 302 is compared with chestpiece 300 in FIG. 3a that air cavity 314 and secondary diaphragm 316 have been added to the chestpiece. The suspension of secondary diaphragm (diaphragm means) 316 is shown as a separate compliant element 317. Second chestpiece air cavity 314 is coupled to the second side of primary diaphragm means 311. Air cavity 314 is also coupled to the first side of secondary diaphragm 316. The second side of secondary diaphragm 316 is coupled to the ambient environment (free air). Secondary diaphragm 316 along with its suspension 317, and second chestpiece air cavity 314 form a second order low pass filter that is located in the transmission path from ambient noise source to the pressure that reaches the second side of primary diaphragm (transducer means) 311.

Figure 4E:
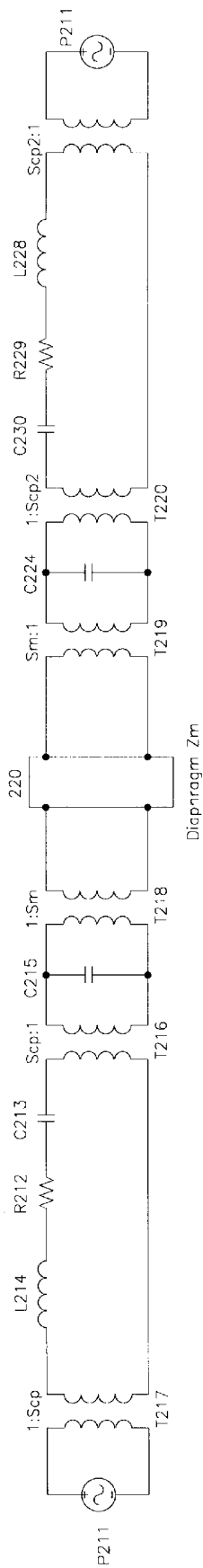
FIG. 4e is an electrical circuit model of the chestpiece of FIG. 3c, where only the response of the system to ambient noise is considered.
Figure 4F:
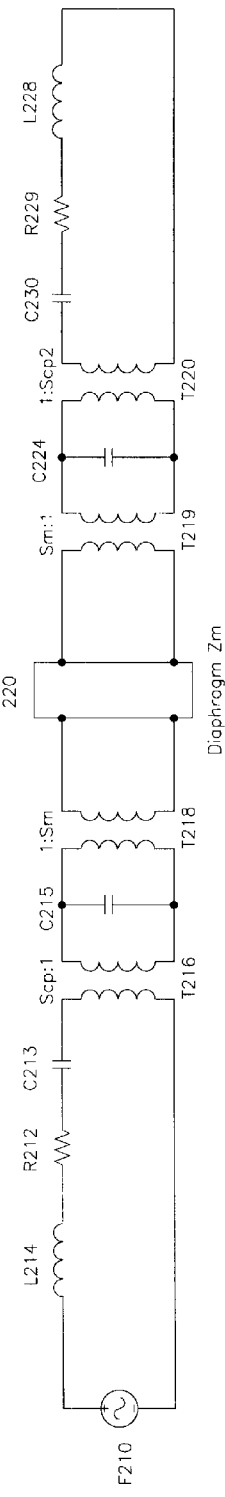
FIG. 4f is an electrical circuit model of the chestpiece of FIG. 3c, where only the response of the system to forces generated by internal physiologic processes are considered.
Figure 5B:
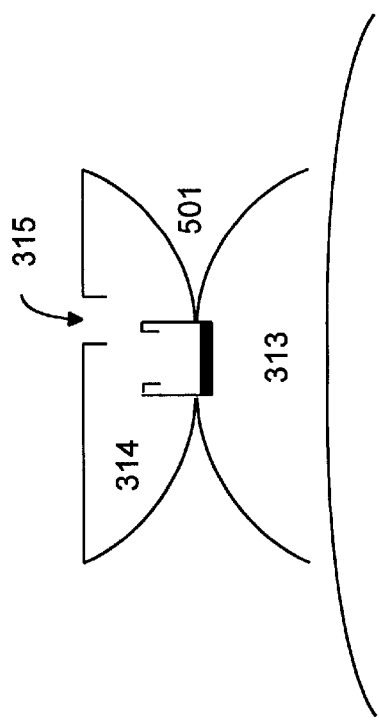
FIG. 5b is a schematic representation of the second chestpiece embodiment of this invention where the first side of the primary diaphragm is coupled to a first chestpiece air cavity and the second side of the primary diaphragm is coupled to a second air cavity, where this second air cavity is coupled to free space through an acoustic mass element, and where the primary diaphragm is the diaphragm of a pressure gradient microphone.
Figure 5D:
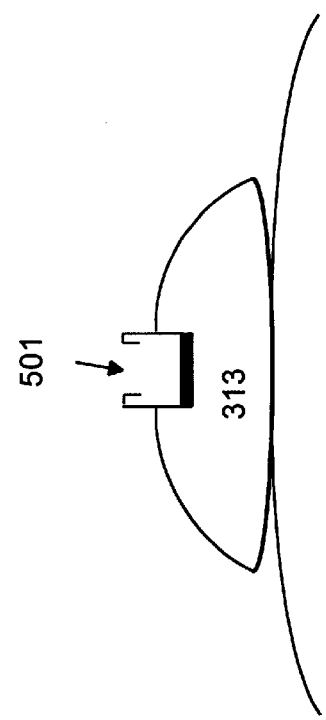
FIG. 5d is a schematic representation of the first chestpiece embodiment of this invention where the first side of the primary diaphragm is coupled to the chestpiece air cavity, the second side of the primary diaphragm is coupled to free space, where the first chestpiece air cavity is coupled to the patient's skin through a traditional diaphragm, and where the primary diaphragm is the diaphragm of a pressure gradient microphone.
Figure 5A:
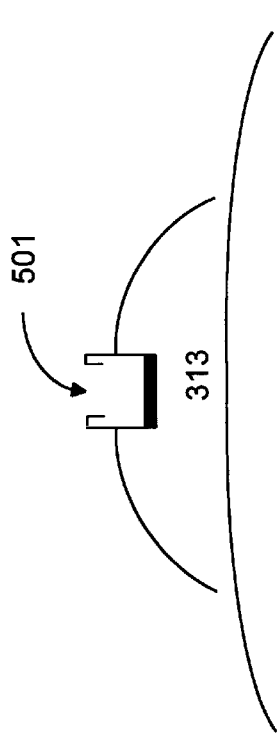
FIG. 5a is a schematic representation of the first chestpiece embodiment of this invention where the first side of the primary diaphragm is coupled to the chestpiece air cavity and the second side of the primary diaphragm is coupled to free space, and where the primary diaphragm is the diaphragm of a pressure gradient microphone.
Figure 5C:
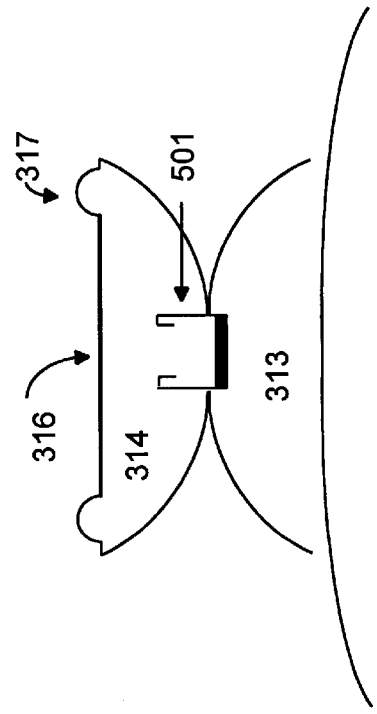
FIG. 5c is a schematic representation of the third chestpiece embodiment of this invention where the first side of the primary diaphragm is coupled to a first chestpiece air cavity and the second side of the primary diaphragm is coupled to a second air cavity, where this second air cavity is coupled to free space through a secondary diaphragm, and where the primary diaphragm is the diaphragm of a pressure gradient microphone.

FIGS. 4e and f give electrical circuit models for the third embodiment chestpiece depicted in FIG. 3c. Circuit 404 of FIG. 4e is a model where only ambient noise is considered. Circuit 405 of FIG. 4f is a model where only forces due to internal physiologic processes are considered. These models can be analyzed separately and the results combined, as the systems are linear and the principal of superposition holds.

The addition of second chestpiece air cavity 314 and secondary diaphragm 316 with suspension 317 result in the additional circuit elements shown to the right of transformer 219 in circuits 404 and 405 of FIGS. 4e and f. Capacitor 224 represents the acoustic compliance of second chestpiece air cavity 314. Inductor 228 represents the mechanical mass of secondary diaphragm 316. Resistor 229 represents the mechanical resistance associated with motion of secondary diaphragm 316. Capacitor 230 represents suspension compliance 317 of secondary diaphragm 316. Transformer 221 represents the coupling of the second side of the secondary diaphragm to the ambient noise present in free air.

It can be seen by looking at FIG. 4e that the topologies of the circuit elements to the left and right sides of primary diaphragm mechanical impedance block 220 are identical. This third embodiment will be capable of the highest degree of cancellation of the component of primary diaphragm motion due to ambient noise. The only limitations on the amount of cancellation achieved will be related to the degree the simplified series resonant model of skin mechanical impedance matches reality, and the ability of the mechanical and acoustical elements coupled to the second side of the primary diaphragm to be tuned to match the behavior of the patient's skin.

Let the transfer function from ambient noise source to pressure applied to the first side of the primary diaphragm be:

$$M(s)=C/e_3(s),$$

and let the transfer function from ambient noise to the second side of the primary diaphragm be:

$$N(s)=D/e_4(s)$$

where $e_3(s)$ and $e_4(s)$ are both second order polynomials in the complex frequency variable s, and C and D are constants. The above approximations are valid if the mechanical impedance of the primary diaphragm is large compared to the other circuit elements. The transfer function from ambient noise source to net pressure applied to the primary diaphragm is then:

$$H_3(s)=M(s)-N(s)=[Ce_4(s)-De_3(s)]/[e_3(s)e_4(s)]$$

The above transfer function has a second order numerator and a fourth order denominator, and is of the same form as the transfer function derived for the second embodiment. It can also be shown that the value of the above transfer function for s=0 is:

$$H_3(s)=[(C_{213}*C_{224})-(C_{230}*C_{215})]/[(C_{213}+C_{215})*(C_{230}+C_{224})],$$

This expression is different than the expression for the second embodiment. It can be seen that the above expression goes to zero if:

$$(C_{213}*C_{224})=(C_{230}*C_{215}).$$

One case where the above condition holds is when the acoustic compliance of the first and second chestpiece air cavities are made equal, and the mechanical compliance of the secondary diaphragm is equal to the mechanical compliance of the patient's skin. (It should be noted that this case is not unique. There are other cases that can also satisfy the above condition). If fact, the entire transfer function can go to zero if in addition the mechanical mass of the secondary diaphragm is equal to the mechanical mass of the patient's skin coupled to the first chestpiece air cavity, and if the mechanical resistance of the secondary diaphragm is equal to the mechanical resistance of the patient's skin (It should be noted that this case also is not unique. There are other cases that can satisfy the above condition). This behavior is in contrast to the behavior of the second embodiment, where it was not possible to choose values for the second chestpiece air cavity 314 compliance, and acoustic element 315 mass and resistance that could make the entire transfer function go to zero.

It is no longer necessary to make the compliance of the chestpiece air cavities small compared to the skin compliance in order to achieve significant levels of attenuation of the component of net pressure applied to the primary diaphragm due to ambient noise. The amount of attenuation achieved for the third embodiment depends on the degree to which the acoustical and mechanical elements coupled to the second side of the primary diaphragm are matched to the mechanical and acoustical elements (skin and first chestpiece air cavity) coupled to the first side of the primary diaphragm. This match can be obtained with any relative relationship between skin compliance and air cavity compliance. This lack of dependence on the compliance ratio of skin to chestpiece air cavity provides additional flexibility in design. The compliances of the chestpiece air cavities can be made larger than in other embodiments, which will increase the difference in the mechanical impedance between the primary diaphragm and the other chestpiece elements. This design methodology can further reduce the interaction of the primary diaphragm with the rest of the chestpiece.

However, the frequency response of the pressure applied to the front of the primary diaphragm due to internal physiologic processes is affected by the absolute magnitudes of the skin and air cavity compliances. In addition, the magnitude of the pressure applied to the front of the primary diaphragm is affected by the ratio of the skin and chestpiece air cavity compliances. This is not a significant difficulty, as these differences in desired body sound frequency response can easily be compensated for by the use of electrical filtering if desired (in embodiments where the primary diaphragm vibration is transduced into an electrical signal).

As was discussed above, the cancellation of the component of primary diaphragm vibration due to ambient noise is maximized when the pressures on each side of the primary diaphragm due to ambient noise are as equal as possible. The second chestpiece air cavity and secondary diaphragm can be designed so that the frequency response of the low pass filter function they apply between ambient noise and the second side of the primary diaphragm matches the frequency response effect of the patient's skin and the first chestpiece air cavity on the ambient noise applied to the first side of the primary diaphragm. However, the mechanical impedance of skin varies from individual to individual. This variation should be accounted for in the chestpiece design to maximize the signal to noise ratio obtained.

It was mentioned above that for the third embodiment, it is not necessary for the chestpiece air cavity compliances to be significantly smaller than the skin compliance, in order for significant attenuation of the effects of ambient noise to occur. However, it will still be desirable for the compliance of the chestpiece air cavities to be small compared to the skin compliance in order to reduce the sensitivity of the system behavior to variation in skin compliance among different individuals.

The effect on system performance from variations in skin compliance among individuals can be minimized but not eliminated, if the first and second chestpiece air cavities are designed to have significantly smaller equivalent mechanical compliances than the average skin mechanical compliance. The earlier discussion concerning the second embodiment with respect to reduction of the effects of skin compliance variation is also applicable here.

It is possible to design a system that can be tuned to compensate for the effects of the variation in skin compliance among individuals. The construction shown in FIG. 10, which was discussed with respect to the second chestpiece embodiment, is also applicable to the third embodiment. This construction allows the user to adjust the volume of the second chestpiece air cavity, which varies the acoustical compliance of the cavity. Adjustment of the compliance of this cavity can compensate for the residual variation in skin compliance.

It will also be desirable for the user to be able to adjust the effective moving mass of the secondary diaphragm. One method for accomplishing this is to alter the acoustical load presented to the side of the secondary diaphragm that is coupled to free space. It is possible to increase the total moving mass of the secondary diaphragm by locating a flat plate above the surface of the diaphragm. The height of this plate above the surface of the secondary diaphragm will affect the mass of air that moves in sympathy with the diaphragm. The presence of the flat plate alters the reactance of the air load impedance seen by the side of the diaphragm exposed to the outside environment. The effect of varying the height of the plate is to vary the effective moving mass of the secondary diaphragm.

An exact expression that relates the change in acoustical mass to the height of a flat plate above the surface of a moving diaphragm is difficult to obtain. Qualitatively, reducing the height of the plate above the surface of the secondary diaphragm will increase the effective moving mass of the secondary diaphragm. The height adjustment can be made into a user control. An example of such a system is shown schematically in FIG. 12. Flat plate 801 is connected to thread assembly 802. Threads 802 mesh with mating threads 803 that are connected to the chestpiece housing 310. Thread assemblies 802 and 803 are not completely solid cylinders. Holes 804 are cut through thread assemblies 802 and 803 to provide an open path from secondary diaphragm 316 to free air. The path through thread assemblies 802 and 803 should be a minimum of 30% open area, with 50% preferably, so that the holes do not restrict the air flow.

It should be noted that adjusting the height of a flat plate above the surface of the secondary diaphragm is not the only method for adjusting the total effective moving mass of the secondary diaphragm assembly. Another method would simply be to add small weights to the surface of the diaphragm. The secondary diaphragm could also be removable, so that different diaphragms with different mechanical impedance could easily be substituted. The invention is not limited in the method used to vary the effective moving mass of the secondary diaphragm.

Sufficient performance can be obtained from the third embodiment without explicitly compensating for the variation in skin mechanical resistance among different individuals, as was the case for the second embodiment. The same method discussed previously for determining the mechanical resistance is also applicable here. The mechanical resistance can be realized in a number of ways. The material used for the diaphragm could be chosen to have a particular mechanical resistance, for the case where a separate compliant suspension for the secondary diaphragm is not used. The resistance could also be made part of the suspension of the secondary diaphragm, when a separate compliant suspension is used. The material chosen for use in the secondary diaphragm suspension would be chosen to have the desired resistance properties (and stiffness). The resistance could also be accomplished acoustically, by placing acoustically absorptive material within the second chestpiece air cavity. Although this provides an acoustical resistance, its effects will be similar to a mechanical resistance included as part of the secondary diaphragm assembly. The amount of absorptive material used will determine the net acoustical resistance provided. Adding more material increases the acoustical resistance.

One design procedure to determine the optimum values for the acoustical and mechanical elements that are coupled to the second side of the primary diaphragm is to: 1) Design the acoustical compliance of the second chestpiece air cavity to match the acoustical compliance of the first chestpiece air cavity, 2) Design the mechanical mass of the secondary diaphragm to match the mechanical mass of the patient's skin, 3) Design the mechanical compliance of the secondary diaphragm to match the mechanical compliance of the patient's skin, and 4) Design the mechanical resistance of the secondary diaphragm to match the mechanical resistance of the patient's skin.

However, the above methodology is not the only design methodology that can be used. The primary requirement that must be met is: 1) The resonant frequency of the skin mechanical mass with the combination of the skin mechanical compliance and equivalent mechanical compliance of the first chestpiece air cavity should match the resonant frequency of the secondary diaphragm mechanical mass with the combination of the secondary diaphragm mechanical compliance and the equivalent mechanical compliance of the second chestpiece air cavity. A secondary requirement that provides further improvement is: 2) The ratio of secondary diaphragm mechanical compliance to the second chestpiece air cavity equivalent mechanical compliance matches the ratio of the skin mechanical compliance to the first chestpiece air cavity equivalent mechanical compliance. A last requirement that will allow a complete matching of the transfer functions is: 3) The mechanical resistance of the secondary diaphragm matches the mechanical resistance of the patient's skin.

The difference between the three requirements above and the first design methodology is that there are a family of component values that can be used to satisfy the above requirements, rather than just one solution. This allows for additional flexibility in the actual design implementation.

Chestpiece 303 in FIG. 3d is identical to chestpiece 300 of FIG. 3a, except for the addition of diaphragm 500. Diaphragm 500 is used in exactly the same manner as diaphragms are used in traditional diaphragm type stethoscopes. Diaphragm 500 couples the patient's skin to the first chestpiece air cavity. The presence of this diaphragm has a small effect on the operation of the system.

The mechanical impedance of diaphragm 500 can be modeled as a series resonant circuit, where the mechanical mass is modeled by an inductor, the mechanical resistance is modeled by a resistor, and the mechanical compliance is modeled by a capacitor. The series resonant circuit that represents the diaphragm mechanical impedance will be in series with the series resonant circuit that models the mechanical impedance of the patient's skin. These elements can be combined into a single series resonant circuit, where the total mechanical resistance is the sum of the individual mechanical resistances, the total mechanical mass is the sum of the individual mechanical masses, and the total stiffness is the sum of the individual stiffnesses (where stiffness is the reciprocal of compliance).

The addition of diaphragm 500 that couples the patient's skin to the first chestpiece air cavity does not alter the system topology in any way. The addition of diaphragm 500 only has the effect of increasing the mechanical mass and resistance, and decreasing the mechanical compliance of the series resonant circuit that models the patient's skin. Therefore, all of the previous analyses done where a bell type chestpiece construction for the first chestpiece air cavity was assumed, are equally applicable when a diaphragm type chestpiece construction is used. The only difference in the various embodiments will be that some of the acoustical and mechanical elements that are coupled to the second side of the primary diaphragm will need to be re-tuned for proper matching. The invention is not limited in the manner in which the first chestpiece air cavity is coupled to the patient's skin.

There are two drawbacks to the use of diaphragm 500. First, the mechanical compliance of diaphragm 500 when combined with the mechanical compliance of the patient's skin, will act to reduce the difference between the effective mechanical compliance of the first chestpiece air cavity and the combined skin and diaphragm 500 mechanical compliances. It was shown earlier that performance improves as this difference increases. Second, the mechanical mass of diaphragm 500 adds to the skin mass, and will reduce the high frequency response of the system to desired sounds.

The effects of the addition of diaphragm 500 can be minimized by making its mechanical compliance large compared the compliance of the first chestpiece air cavity. Performance is further improved if the compliance of diaphragm 500 is large compared to the skin compliance, although this may be difficult to achieve in practice. The effects are also minimized if the mass of diaphragm 500 is kept as small as possible.

It can be seen that there are no real acoustic performance advantages to the use of a diaphragm type first chestpiece air cavity over the use of a bell type cavity. There are, however, a number of practical benefits to a diaphragm type design. When diaphragm 500 is used, it will seal the first side of the primary diaphragm from the external environment. This will protect the primary diaphragm. Diaphragm 500 can be designed so that it provides physical protection against damage, and environmental protection against corrosion and the effects of chemical contaminants. The second benefit to the use of diaphragm 500 is that it provides an air seal for cavity 313 under all conditions. The edge of chestpiece body 310 does not need to contact the patient's skin around its entire circumference in order provide an air seal for the first chestpiece air cavity 313. This behavior is useful for cases where it is necessary to monitor a patient through clothing, where a complete air seal may not otherwise be possible.

Transduction Methods

The various chestpiece embodiments include some form of transducer means. The transducers are designed to output a signal that is proportional to an acoustic pressure difference between two points in space. The chestpieces are constructed so that the transducers are responsive to the pressure difference between the air pressure variations in the first chestpiece air cavity, and the air pressure variation due to ambient noise present in the environment.

One method of achieving a transducer that is responsive to the pressure difference between two points in space is to separate the two points in space with a diaphragm that is free to move. The pressure difference is transformed by the diaphragm into a force difference. This force difference will cause the diaphragm to move in response. This motion can then be further transduced into whatever form is desired for additional processing.

The chestpiece embodiments of this disclosure employ a primary diaphragm to convert a pressure difference into a force difference. The pressure applied to the first side of the primary diaphragm is due to vibration of the patient's skin (which has a component due to internal physiologic processes and a component due to ambient noise). At the same time, a pressure is also applied to the second side of the primary diaphragm, where this pressure is due only to ambient noise. The net force applied to the primary diaphragm is proportional to the pressure difference applied to the first and second sides of the diaphragm. The vibration of the primary diaphragm is proportional to the net force applied. The resulting motion of the primary diaphragm will be analogous to the component of the patient's skin vibration that is due only to internal physiologic processes.

In order for this system to be useful as a stethoscope, the resulting primary diaphragm motion must be converted into an acoustical signal that can be presented to the user's ears. This can be done by first transducing the diaphragm motion into an intermediate form, such as an electrical signal. This intermediate signal can then be manipulated as desired, and ultimately transduced into an acoustic pressure that is transmitted to the user's ears. The vibration signal could also be directly transduced into an acoustic signal which could be conducted through tubes to the user's ears, as is done in traditional stethoscopes.

There are numerous methods that can be used to transduce the vibration of the primary diaphragm into an electrical signal. The diaphragm's displacement, velocity, or acceleration could be transduced. Transduction methods can include use of piezoelectric, piezoresistive, or electromagnetic effects, as well as a host of other methods such as variable capacitance, optical, ultrasonic, RF, etc. The invention is not limited in the quantity that is transduced (displacement, velocity, or acceleration) or the method used to transduce the vibration of the primary diaphragm into an electrical signal. In many of these transduction methods, a part of the transducer itself performs the function of the primary diaphragm. The primary diaphragm does not need to be a separate element to which separate transducer means are attached. The primary diaphragm can be integral to the transducer used.

There are certain transduction methods that have particular appeal. It was stated earlier that the mechanical impedance of the primary diaphragm should be large compared to the other system elements, and that reducing the diaphragm area was beneficial to reducing interaction effects. The diaphragm mechanical impedance can be large if its mass is small and its compliance is small. The requirements of small area, low mass and high stiffness are all compatible with basic microphone transduction methods. In fact microphones are specifically designed to have these characteristics so that they have a minimal influence on the pressure field they are transducing.

The transduction of the motion of a diaphragm into an electrical signal, where the diaphragm motion is responsive to the pressure difference between the front and rear sides of the diaphragm, and where the diaphragm is small, light weight and stiff, is an accurate description of a pressure gradient microphone. Pressure gradient microphones are also known as dipole microphones (or sometimes noise canceling microphones), where dipole describes the shape of the microphone pickup pattern as a function of the direction of arrival of sound. A dipole pickup pattern has a figure eight shape. Pressure gradient microphones have opposite polarity outputs for pressures applied to the different sides of the diaphragm.

Pressure gradient microphones with small, stiff, light weight diaphragms and high conversion efficiency from applied differential pressure to electrical signal output are readily available. An example of such a device is the Panasonic WM-55D103 noise canceling back electret condenser microphone cartridge. The use of a pressure gradient microphone in the three primary embodiments of the current invention was first disclosed in the author's previous U.S. Pat. No. 5,492,129. Chestpiece configurations according to the present invention using pressure gradient microphones as the transducer means are shown in FIGS. 5a–d.

The configurations shown in FIGS. 5a–d all have pressure gradient microphone 501 mounted so that the front of pressure gradient microphone 501 is coupled to the first chestpiece air cavity 313, and the back of pressure gradient microphone 501 is either directly coupled to free air, or is coupled to second chestpiece air chamber 314. It should be noted that the pressure gradient microphone will transduce the same pressure signal that physicians are accustomed to hearing, when used as shown. This is an important point. This transduction method will allow the reproduction of body sound signals in the manner that physicians are accustomed to hearing. This means that physicians will not require any retraining in order to use the electronic stethoscope.

A pressure gradient microphone can be approximated by the use of two pressure microphones located close to each other, where the polarity of the output of one microphone is reversed with respect to the other microphone, and the outputs of the two microphones are summed together. Two separate pressure microphones can be used everywhere a single pressure gradient microphone appears. There are however, advantages to using a single pressure gradient microphone. First, only one microphone element is needed. Second, the pressure gradient microphone will have inherently lower output signals due to ambient noise than the pair of pressure microphones. The cancellation of ambient noise happens acoustically, and transduction occurs after cancellation with a pressure gradient microphone. When a pair of pressure microphones are used, cancellation is done electrically and transduction occurs before cancellation. The headroom and signal to noise ratio of a system employing a pressure gradient microphone are inherently higher than systems employing a pair of pressure microphones.

In addition, the transfer function of the individual microphones will have an effect on the total amount of cancellation achievable when two separate microphones are used. Any mismatches in the transfer functions of the individual microphones will limit the maximum cancellation obtained. The transfer functions from an external noise source to the front and back of a pressure gradient microphone are inherently better matched than the transfer functions from the same external noise source to two separate pressure microphones.

Mechanical Transduction of Primary Diaphragm Vibration

It was mentioned previously that the pressure difference between the air pressure in the first chestpiece air cavity and ambient noise could be directly transduced into an acoustic pressure, which could then be conducted through tubes to the user's ears. This system relies on a primary diaphragm used in a similar manner to the various embodiments shown in FIGS. 3a–d. These embodiments provide a primary diaphragm whose vibration has an increased signal to noise ratio as compared to the vibration of the patient's skin. It is possible to transduce the vibration of this diaphragm into an acoustic signal, in a similar manner to how a traditional stethoscope transduces skin vibration into an acoustical signal.

Figure 6A:
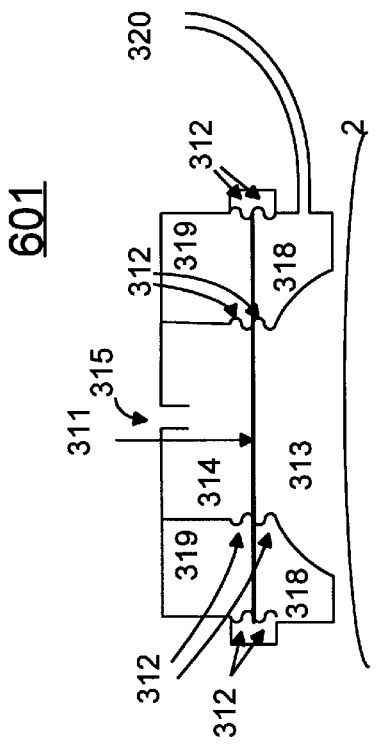
FIG. 6a is a schematic representation of the first chestpiece embodiment of FIG. 3a when used in a mechano-acoustic stethoscope.
Figure 6B:
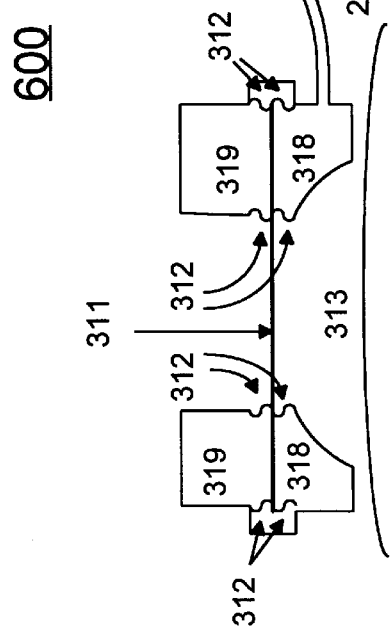
FIG. 6b is a schematic representation of the second chestpiece embodiment of FIG. 3b when used in a mechano-acoustic stethoscope.
Figure 6C:
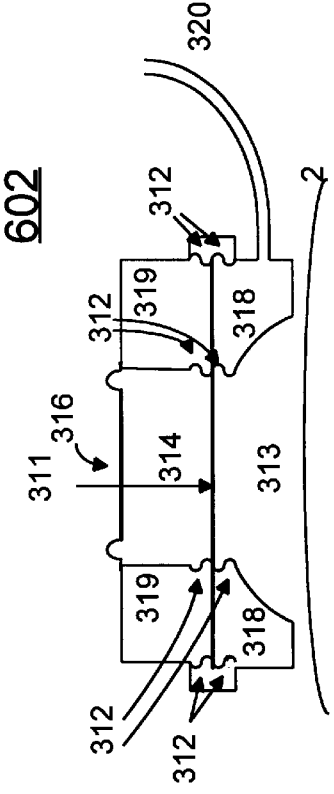
FIG. 6c is a schematic representation of the third chestpiece embodiment of FIG. 3c when used in a mechano-acoustic stethoscope.

In order to transduce the primary diaphragm vibration into an acoustic signal, an additional air cavity or chamber is coupled to the primary diaphragm. When the primary diaphragm moves, it generates a pressure variation in this cavity. This pressure variation is then conducted through tubes coupled to the additional cavity, to the user's ears. Various construction methods for such a device are shown in FIGS. 6a–c. Primary diaphragm 311 in FIGS. 6a–c has a diameter that extends beyond the area where first chestpiece air cavity 313 and second chestpiece air cavity 314 (if present) couple to the primary diaphragm.

Primary diaphragm 311 should be light weight and extremely stiff. The forces applied over the areas where the primary diaphragm is coupled to the first and second cavities must by conducted by the primary diaphragm to additional air cavities 318 and 319. The first bending mode frequency of the primary diaphragm should be above the frequency range of interest (above approximately 1.5 Khz). FIGS. 6a–c also show a number of compliant elements 312 that couple the primary diaphragm at various locations to chestpiece body 310. The mechanical compliance of compliant elements 312 should be as large as practical, so that they have minimal influence on the vibration of the diaphragm. The primary purpose of compliant elements 312 is to provide an air seal between the primary diaphragm and the various air cavities in the chestpiece structure, while not impeding the vibration of the primary diaphragm.

Chestpieces 600–603 in FIGS. 6a–c show two additional air cavities or chambers 318 and 319 coupled to the primary diaphragm. Air cavity 318 is shown connected through tubes 320 to the user's ears. Air cavity 319 functions to isolate the portion of the primary diaphragm that couples to air cavity 318 from all other acoustic pressure sources. The air cavity that is coupled to the user's ears (cavity 318 in chestpieces 600–603) should be significantly smaller than the second additional cavity (cavity 319 in chestpieces 600–603). The majority of the stiffness applied to the primary diaphragm should be contributed by the acoustical compliance of the air cavity that is coupled to the user's ears. The acoustic compliance of cavity 318 should be significantly smaller than the acoustic compliance of cavity 319. The ratio of the combined effective mechanical compliance of suspension elements 312 and cavity 319 to the effective mechanical compliance of cavity 318 directly affects the efficiency of the transduction of the primary diaphragm vibration into an acoustic signal.

It should be noted that cavity 319 could be made the smaller of the two cavities, and it could be connected through tubes to the user's ears if desired. There is no significant difference to having the smaller air cavity being coupled to the first or second side of the primary diaphragm.

Alternative constructions for the mechanical systems of FIGS. 6a–c are shown are FIGS. 7a–c. The fundamental difference between the construction methods of FIGS. 7a–c and those shown in FIGS. 6a–c are that: A) only additional air cavity 318 is used, and B) the area of the primary diaphragm that is coupled to ambient noise, either directly or through the second chestpiece air cavity is different from the area of the primary diaphragm coupled to the first chestpiece air cavity.

The force applied to the first side of the primary diaphragm depends on the pressure developed in the first chestpiece air cavity, and the area of the primary diaphragm that is coupled to this cavity. The force applied to the second side of the primary diaphragm depends on the pressure present at the second side of the primary diaphragm, and the area of the diaphragm over which this pressure is present. The real functional difference between the two constructions is the difference in coupling areas to the first and second sides of the primary diaphragm. It can be seen that a difference in coupling area can result in a difference in the force applied.

In the first two embodiments, this area difference, and the resulting force difference, could actually be used to advantage. In the third embodiment, an area difference would be a disadvantage. It was mentioned earlier that the topologies of the elements in the transmission paths from ambient noise source to the first and second sides of the primary diaphragm do not match for the first and second embodiments. In the second embodiment, the acoustical and mechanical filter elements can be chosen to match the shape of the frequency response of the transfer function from ambient noise to the first side of the primary diaphragm. However, when the frequency response shape is matched, there will be a level mismatch. There is both a level mismatch and a shape mismatch in the first embodiment where there are no acoustical or mechanical elements coupled to the second side of the primary diaphragm.

The source of the level mismatch can be seen in the electrical circuit models of FIGS. 4a–d. The voltage across capacitor 215 is analogous to the pressure developed in the first chestpiece air cavity. There is a voltage division that occurs between capacitor 213, which represents the skin mechanical compliance, and capacitor 215. There is no such voltage division occurring in the transmission path from ambient noise to the second side of the primary diaphragm. What this implies is that for the transmission path from ambient noise to the pressure applied to the first side of the primary diaphragm, the force developed due to ambient noise impinging on the skin is divided into compressing the skin and compressing the first chestpiece air cavity. That is, not all of the force developed from the ambient noise pressure goes into developing a pressure in the first chestpiece air cavity. There is no such splitting of applied forces or applied pressures in the transmission path from the ambient noise source to the second side of the primary diaphragm. It is this level mismatch can be compensated for by scaling the coupling area between the primary diaphragm the first and second air cavities.

In the third embodiment, it was mentioned that the topologies of the elements in the transmission path from ambient noise to the first side of the primary diaphragm match the topology of the elements in the transmission path from ambient noise to the second side of the primary diaphragm. In this case, there will be no level mismatch if the ratio of the second chestpiece air cavity equivalent mechanical compliance to the secondary diaphragm mechanical compliance matches the ratio of the first chestpiece air cavity equivalent mechanical compliance to the skin mechanical compliance. The third embodiment does not have a need to adjust the relative coupling areas. However, the construction method shown in FIG. 7c can still be used. The compliance ratio of the second chestpiece air cavity to the secondary diaphragm compliance could be adjusted to compensate for the area difference.

Electrical circuit models for the chestpiece embodiments shown in FIGS. 6a–c are given in FIGS. 8a–f. The electric circuit models in FIGS. 8a–f are analogous to the models given in FIGS. 4a–f. The primary difference is that diaphragm mechanical impedance block 220 of FIGS. 4a–f has been replaced by circuit elements that model the primary diaphragm, the suspension compliances, and the additional air cavities. Inductor 610 represents the mechanical mass of the primary diaphragm. Resistor 611 represents the mechanical resistance of the primary diaphragm suspension. Capacitor 612 represents the mechanical compliance of suspension elements 312. Capacitor 618 represents the equivalent mechanical compliance of air cavity 318. Capacitor 619 represents the equivalent mechanical compliance of air cavity 319. (The acoustical compliances of cavities 318 and 319 have been reflected into the mechanical domain for clarity.)

The model for the primary diaphragm and the associated cavities is a series resonant circuit. The variable of interest is the voltage across capacitor 318. This quantity represents the force applied to the equivalent mechanical compliance of the air cavity that is connected to the user's ears. It is related to the pressure developed in air cavity 318 through a scale factor (the square of the diaphragm area coupled to the cavity). The fundamental design goal is for the series resonant circuit representing the primary diaphragm, air cavities 318 and 319, and suspension elements 312 to have a large mechanical impedance compared to the other circuit elements, over the frequency range of interest (which is approximately 10 Hz to 1.5 Khz). This will minimize the interaction of the diaphragm with the other elements. A high mechanical impedance can be accomplished by minimizing the mass of the primary diaphragm, and minimizing the total mechanical compliance of the three series connected compliances.

It was mentioned above that the voltage across capacitor 618 is related to the pressure developed in air cavity 318. It is desired to maximize this quantity. Therefore, the compliance of this cavity should be small compared to the other system compliances. This translates to the requirement that the impedance of capacitor 318 should be large compared to the other element impedances.

Figure 8A:
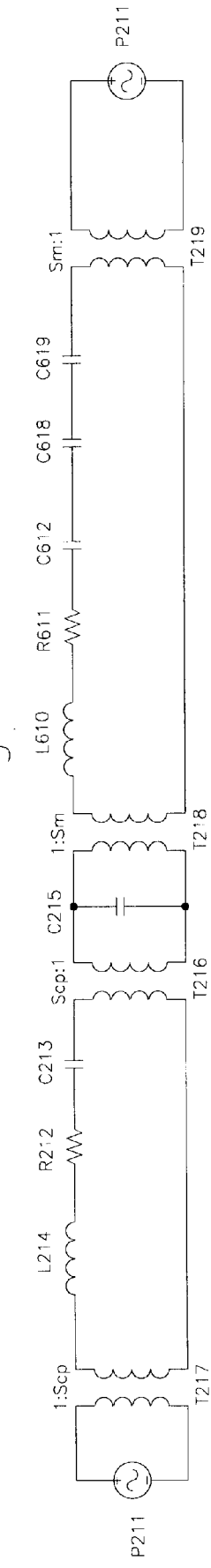
FIG. 8a is an electrical circuit model of the system of FIG. 6a, where only the response of the system to ambient noise is considered.
Figure 8B:
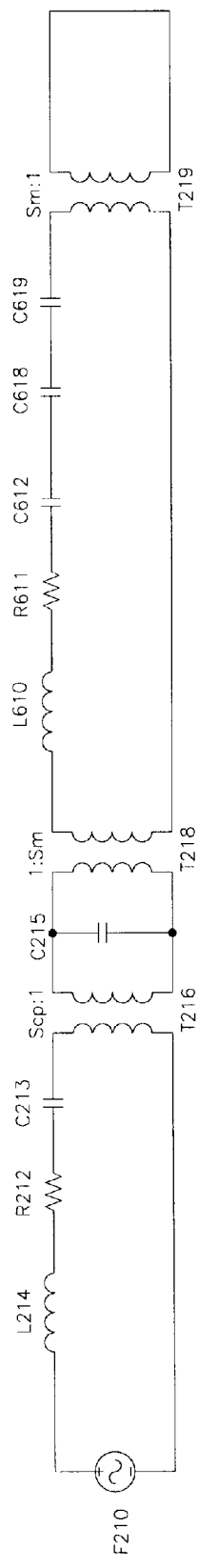
FIG. 8b is an electrical circuit model of the system of FIG. 6a, where only the response of the system to forces generated by internal physiologic forces are considered.
Figure 8C:
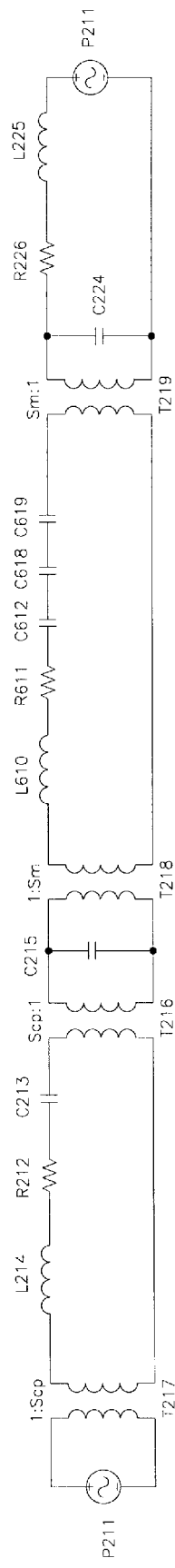
FIG. 8c is an electrical circuit model of the system of FIG. 6b, where only the response of the system to ambient noise is considered.
Figure 8D:
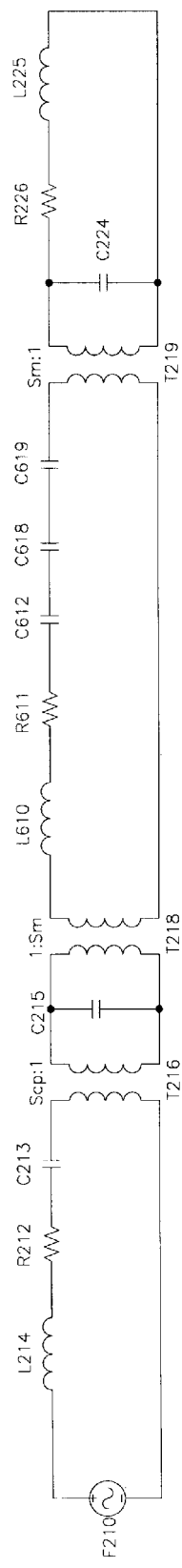
FIG. 8d is an electrical circuit model of the system of FIG. 6b, where only the response of the system to forces generated by internal physiologic forces are considered.
Figure 8E:
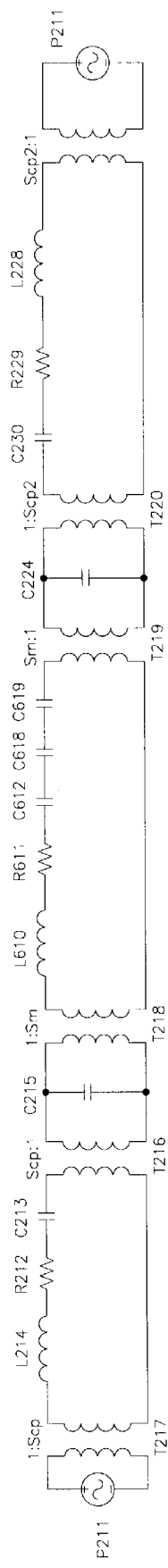
FIG. 8e is an electrical circuit model of the system of FIG. 6c, where only the response of the system to ambient noise is considered.
Figure 8F:
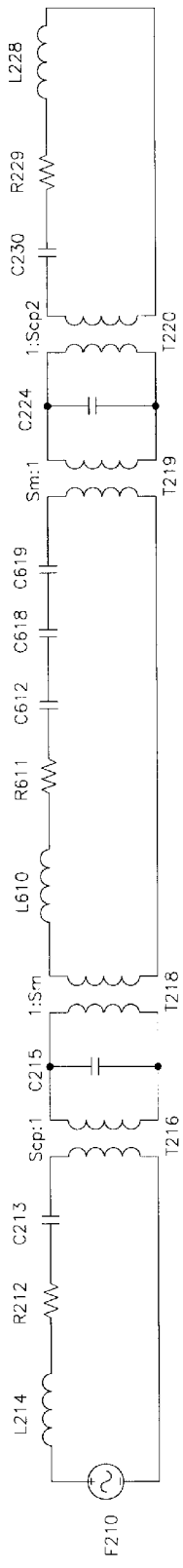
FIG. 8f is an electrical circuit model of the system of FIG. 6c, where only the response of the system to forces generated by internal physiologic forces are considered.

The electrical circuit models given in FIGS. 8a–c are also directly applicable to the alternative constructions shown in FIGS. 7a–c. The element topologies are virtually identical. The primary difference is that capacitor 619 is omitted (only one extra air cavity is coupled to the primary diaphragm). One other difference will be that the turns ratio of transformer 219 will change to account for the reduction of area coupled to the second chestpiece air cavity (or ambient noise for the construction of FIG. 7a).

FIGS. 7a–c show air cavity 318 coupled to the second side of the primary diaphragm. It should be noted here that this air cavity could also be coupled to the first side of the primary diaphragm if desired. This configuration, while it can be made to work, will not perform as well, when used in the first two embodiments, as the configurations shown in FIGS. 7a–b. The change in the coupling areas is in the opposite direction from what is desired to compensate for the voltage division effect described earlier. Coupling cavity 318 to the first side of the primary diaphragm can be compensated for by adjusting the relative compliances of the second chestpiece air cavity and the secondary diaphragm compliance ratio in the third embodiment.

The design methodologies described earlier for determining the values of the various elements that are coupled to the second side of the primary diaphragm are directly applicable to the mechanical transduction methods described here.

Active Noise Cancellation

The application of active noise cancellation (ANC) to a stethoscope was described in the author's previous U.S. Pat. No. 5,492,129. The basic principle behind the application of active noise reduction to a stethoscope is straightforward. The desired body sound signal is transduced by a first sensor. When ambient noise is present, the output of the body sound sensor will have a component due to internal physiologic processes and a component due to ambient noise. The purpose of the ANC system is to remove the ambient noise component of the body sound sensor output while leaving the desired body sounds unaltered. A second sensor is used in an ANC system. This sensor is arranged so that it is only exposed to ambient noise. The output of the noise sensor is then passed through a filter, and the output of the filter is subtracted from the output of the body sound sensor. The transfer function of the filter can be time variant or time invariant (adaptive or fixed), and the signal processing can be analog or digital.

Let the transfer function from the ambient noise source to the output of the body sound sensor be $H_1(s)$. Let the transfer function from ambient noise source to the output of the ambient noise sensor be $H_2(s)$. Let the transfer function of the filter that is in the signal path of the ambient noise sensor be $H_3(s)$. The component of the body sound sensor output due to ambient noise will be canceled completely when the following condition holds:

$$H_3(s) = H_1(s)/H_2(s)$$

In an active adaptive noise canceling system, the filter in the signal path of the ambient noise sensor has a time varying transfer function. An adaptive algorithm is used to adapt the filter frequency response, where the algorithm adjusts the filter in an attempt to satisfy the above condition. A typical adaptive system uses an adaptive FIR digital filter, and a gradient based adaptive algorithm (such as the well known LMS algorithm), but many other system configurations are possible.

Due to the nature of the adaptive algorithm used, the match of the topology of the time varying filter to the underlying system, and various non idealities in the overall system (such as finite precision arithmetic, DC offsets, etc.), the ability of an adaptive filter to satisfy the fine details of the above condition is limited. The amount of noise cancellation that an adaptive noise cancellation system can achieve is limited.

The performance of a stethoscope in the presence of noise directly depends on the signal to noise ratio of the signal that is presented to the user's ears. The system performance will be improved if the inherent signal to noise ratio of the body sound sensor is improved, before it is applied to an adaptive noise canceling system. The new chestpiece configurations that are the subject of the current invention are ideally suited to act as body sound sensors in an ANC stethoscope system. The increased noise attenuation provided by the new chestpiece embodiments is added to the noise attenuation provided by the ANC electronics, to improve the total system performance. It should be noted that the use of the chestpiece embodiments of the current invention are not limited in any way to the type of active noise cancellation system they are used with.

Figure 9D:
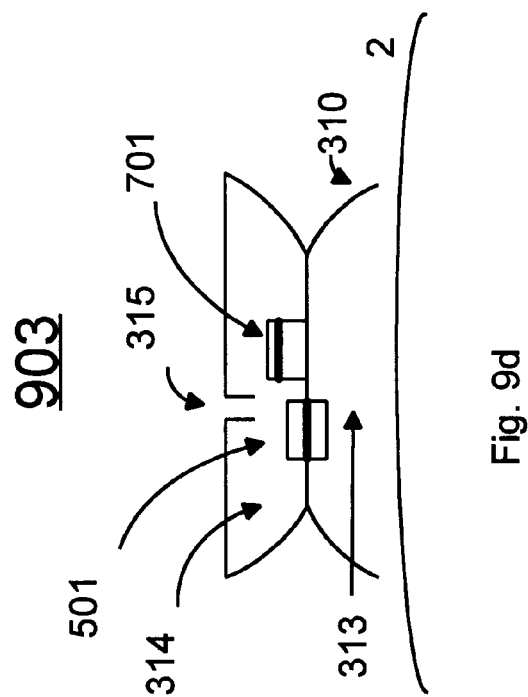
FIG. 9d is a schematic representation of the second chestpiece embodiment of this invention used as a body sound sensor, with an added ambient noise sensor located in the second chestpiece air cavity, for use with an active noise cancellation stethoscope.
Figure 9E:
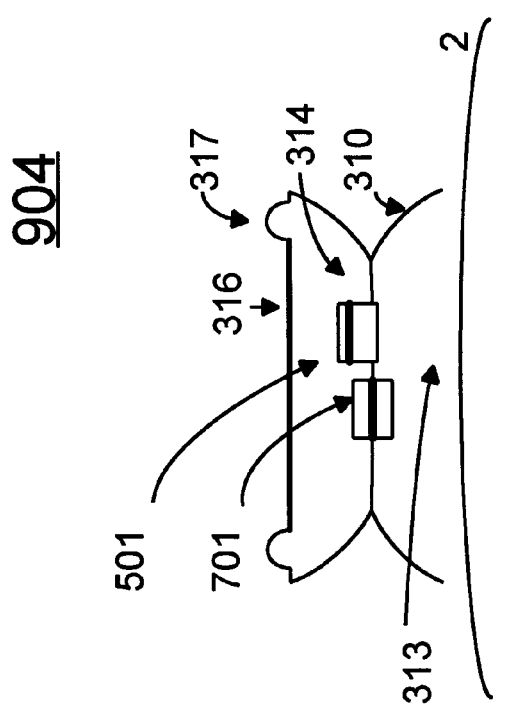
FIG. 9e is a schematic representation of the third chestpiece embodiment of this invention used as a body sound sensor, with an added ambient noise sensor located in the second chestpiece air cavity, for use with an active noise cancellation stethoscope.

The configurations shown in FIGS. 5a–d can be modified for use with an ANC system. The chestpieces in FIGS. 5a–d use a pressure gradient microphone as the primary transducer. The pressure gradient microphone will serve as the body sound sensor in the new ANC stethoscopes. An ambient noise sensor is also required for an ANC system. Schematic representations of chestpieces that use the embodiments of this invention as a body sound sensor, and include a second ambient noise sensor are shown in FIGS. 9a–e. In FIG. 9a, ambient noise sensor 701 is shown located outside of the first chestpiece air cavity 313, in close proximity to pressure gradient microphone 501. The preferred location for ambient noise sensor 701 for this configuration is directly above the rear of pressure gradient microphone 501. The close proximity of the sensors reduces the phase difference between the signals transduced by each of the sensors. This will improve the noise cancellation obtained. In FIGS. 9b and c, ambient noise sensor 701 is shown exposed to free space, attached to chestpiece body 310. The location shown for ambient noise sensor is not the only possible location. It could be located virtually anywhere on the chestpiece assembly (on top for example) with no significant change in performance, as long as it is exposed to free air.

In FIGS. 9d and e, ambient noise sensor 701 is shown located inside second chestpiece air cavity 314. Ambient noise sensor 701 will still be exposed primarily to ambient noise, as the mechanical impedance of pressure gradient microphone 501 is high, and very little sound energy will be transmitted from the first chestpiece air cavity 313 through pressure gradient microphone 501 into the second chestpiece air cavity 314. This is a critical point. Any sound transmission from the first chestpiece air cavity into the second chestpiece air cavity will limit the maximum amount of noise cancellation that can be achieved. A high mechanical impedance for the primary diaphragm is required for maximum cancellation in and ANC system.

There are a number of benefits to locating the noise sensor in the second chestpiece air cavity. The first is that the order of the noise cancellation filter in the ANC system required for optimum noise cancellation is reduced. It was stated earlier that the transfer function from ambient noise source to net pressure applied to the primary diaphragm, for both the second and third embodiments, had a second order numerator and a fourth order denominator. One pair of poles in the denominator are due to the acoustical and mechanical filter elements that are coupled to the second side of the primary diaphragm. The transfer function from ambient noise source to the output of the ambient noise sensor, when it is located inside the second chestpiece air cavity, will have a second order denominator, where the pole pair exactly matches the pole pair in the denominator of the transfer function mentioned above. The active noise cancellation system will no longer need to model this part of the system. Therefore, the order of the noise cancellation filter needed to maximize cancellation achieved by the ANC system is lower when the ambient noise microphone is located within the second chestpiece air cavity.

An additional benefit is that the ambient noise microphone can be more easily protected from mechanical damage, and from the environment. When the third embodiment chestpiece is used, and when diaphragm 500 is used to couple the first chestpiece air cavity to the patient's skin, both of the transducers used can be protected.

Reference Patents

U.S. Pat. No. 5,539,831 Active Noise Control Stethoscope Harley, Thomas R.

U.S. Pat. No. 5,492,129 Noise Reducing Stethoscope Greenberger, Hal P.

U.S. Pat. No. 4,458,778 Stethoscope Construction Bloom, Max

U.S. Pat. No. 2,389,868 Acoustic Stethoscope Olson, Harry F.

References

1. Noise and Vibration Control Engineering, Edited by Leo L. Beranek, Istvan L. Ver, 1992 John Wiley and Sons.

2. Dynamical Analogies Harry F. Olson D. Van Nostrand Company, New York.

Although specific features are shown in some drawings and not others, this is for convenience only, as each feature may be combined with any or all of the other features in accordance with the invention.

Other embodiments will occur to those skilled in the art and are within the following claims:

What is claimed is:

1. A stethoscope chestpiece for transducing skin vibrations due to internal physiologic processes of a patient with an increased signal to noise ratio, comprising:

a first air cavity adapted to be coupled to skin;

diaphragm means with a front side and a rear side, in which the front side of the diaphragm means is coupled to the first air cavity, and the rear side of the diaphragm means is coupled to free air, where the diaphragm means is set back from the patient's skin so that there is no direct physical contact between the front side of the diaphragm means and the patient's skin, so that the only forces available to act on the diaphragm means are due to the air pressure present at the front and rear sides of the diaphragm means, and;

transducer means coupled to the diaphragm means, wherein the transducer means outputs a signal in response to the vibration of the diaphragm means, where the vibration of the diaphragm means is due to the air pressure difference between the front and rear sides of the diaphragm means.

2. The stethoscope chestpiece of claim 1 in which the combination of diaphragm means and transducer means is comprised of a pressure gradient microphone.

3. The stethoscope chestpiece of claim 1 in which the diaphragm means has high mechanical impedance.

4. The stethoscope chestpiece of claim 1 where the transducer means converts the vibration of the diaphragm means into an electrical signal.

5. The stethoscope chestpiece of claim 1 further including means for directly converting the vibration of the diaphragm means into an acoustic pressure signal.

6. The stethoscope chestpiece of claim 5, in which the means for directly converting the vibration of the diaphragm means into an acoustic pressure signal includes:

a second air cavity, coupled to either side of the diaphragm means and not otherwise coupled to free air; and a tube assembly, coupled to the second air cavity, for conducting the air pressure signal present in the second air cavity to the user's ears.

7. The stethoscope chestpiece of claim 5, in which the means for directly converting the vibration of the diaphragm means into an acoustic pressure signal includes:
   a second air cavity coupled to one side of the diaphragm means;
   a third air cavity coupled to the other side of the diaphragm means, in which the third air cavity is otherwise sealed from all other air cavities in the chestpiece assembly, and is also sealed from free air; and
   a tube assembly, coupled to the second air cavity, for conducting the air pressure signal present in the second air cavity to the user's ears.

8. The stethoscope chestpiece of claim 1 further including:
   a noise sensor for detecting ambient noise proximate to the transducer means, which outputs a noise signal;
   filter means for filtering the noise signal; and
   means for subtracting the filtered noise signal from the transducer means output signal, to reduce the component due to ambient noise in the transducer means output signal.

9. The stethoscope chestpiece of claim 1 further including:
   a second diaphragm means with a front side and a rear side, wherein the front side of the second diaphragm means is arranged so that it comes into direct contact with the patient's skin, and the rear side of the second diaphragm means is coupled to the first air cavity, where the second diaphragm means is arranged so that it does not come into direct physical contact with the first diaphragm means.

10. A stethoscope chestpiece for transducing skin vibrations due to internal physiologic processes of a patient with an increased signal to noise ratio, comprising:
   a first air cavity adapted to be coupled to the skin;
   an acoustical mass coupled to free air;
   an acoustical resistance coupled to free air;
   a second air cavity coupled to both the acoustical mass and the acoustical resistance;
   diaphragm means with a front side and a rear side, in which the front side of the diaphragm means is coupled to the first air cavity, and the rear side of the diaphragm means is coupled to the second air cavity, where the diaphragm means is set back from the patient's skin so that there is no direct physical contact between the front side of the diaphragm means and the patient's skin, so that the only forces available to act on the diaphragm means are due to the air pressure present at the front and rear sides of the diaphragm means, and;
   transducer means coupled to the diaphragm means, wherein the transducer means outputs a signal in response to the vibration of the diaphragm means, where the vibration of the diaphragm means is due to the air pressure difference between the front and rear sides of the diaphragm means.

11. The stethoscope chestpiece of claim 10 in which the combination of the diaphragm means and the transducer means is comprised of a pressure gradient microphone.

12. The stethoscope chestpiece of claim 10 in which the diaphragm means has high mechanical impedance.

13. The stethoscope chestpiece of claim 10 further including means for converting the vibration of the diaphragm means into an electrical signal.

14. The stethoscope chestpiece of claim 10 further including means for directly converting the vibration of the diaphragm means into an acoustic pressure signal.

15. The stethoscope chestpiece of claim 14, in which the means for directly converting the vibration of the diaphragm means into an acoustic pressure signal includes:
   a third air cavity, coupled to the diaphragm means and not otherwise coupled to free air; and
   a tube assembly, coupled to the third air cavity for conducting the air pressure signal present in the third air cavity to the user's ears.

16. The stethoscope chestpiece of claim 14, in which the means for directly converting the vibration of the diaphragm means into an acoustic pressure signal includes:
   a third air cavity coupled to one side of diaphragm means;
   a fourth air cavity coupled to the other side of diaphragm means, in which the fourth air cavity is otherwise sealed from all other air cavities in the chestpiece assembly, and is also sealed from free air; and
   a tube assembly, coupled to the third air cavity, for conducting the air pressure signal present in the third air cavity to the user's ears.

17. The stethoscope chestpiece of claim 10 further including means for providing user adjustment of the acoustic compliance of the second air cavity.

18. The stethoscope chestpiece of claim 17 further including means for providing user adjustment of the magnitude of the acoustical mass.

19. The stethoscope chestpiece of claim 10 further including means for user adjustment of the magnitude of the acoustical mass.

20. The stethoscope chestpiece of claim 10 further including:
   a noise sensor for detecting ambient noise proximate the transducer means, which outputs a noise signal;
   filter means for filtering the noise signal; and
   means for subtracting the filtered noise signal from the transducer means output signal, to reduce the component due to ambient noise in the transducer means output signal.

21. The stethoscope of claim 10 further including;
   diaphragm means with a front side and a rear side, wherein the front side of the diaphragm means is arranged so that it comes into direct contact with the patient's skin, and the rear side of the diaphragm means is coupled to the first air cavity, where the second diaphragm means is arranged so that it does not come into direct physical contact with the first diaphragm means.

22. A stethoscope for transducing skin vibrations due to internal physiologic processes of a patient with an increased signal to noise ratio in the presence of ambient noise, comprising:
   a chestpiece including:
      a first air cavity adapted to be coupled to the skin;
      a first diaphragm means with a front side and a rear side, where the front side of the first diaphragm means is coupled to the first air cavity and set back from the patient's skin so that no portion of the diaphragm means comes in direct physical contact with the patient's skin, so that the only forces available to act on the diaphragm means are due to the air pressure present at the front and rear sides of the diaphragm means; and
      transducer means coupled to the diaphragm means, wherein the transducer means outputs a signal in response to the vibration of the diaphragm means, where the vibration of the diaphragm means is due to the air pressure difference between the front and rear sides of the diaphragm means, and;

means for presenting the transducer means output signal to the user's ears.

23. The stethoscope of claim 22 further including:

a noise sensor for detecting ambient noise proximate the chestpiece, which outputs a noise signal;

filter means for filtering the noise signal; and means for subtracting the filtered noise signal from the output signal, before presenting the output signal to the user's ears.

24. The stethoscope of claim 23 in which the filter means has a time invariant transfer function.

25. The stethoscope of claim 23 in which the filter means has a time variant transfer function, and further includes an adaptive algorithm to adapt the filter means frequency response.

26. The stethoscope of claim 22, where the chestpiece further includes:

a second air cavity, coupled to the rear side of the first diaphragm means;

an acoustical mass, coupled between the second air cavity and free air; and an acoustical resistance, coupled between the second air cavity and free air;

wherein the first diaphragm means is arranged so that the air pressure applied to the rear side of the first diaphragm means is the pressure present within the second air cavity;

wherein the transducer means outputs a signal in response to the vibration of the first diaphragm means, where the vibration of the first diaphragm means is due to the difference in air pressure between the first and second cavities, where the pressures in the first and second cavities act on the front and rear sides of the first diaphragm means respectively.

27. The stethoscope of claim 26 further including:

a second diaphragm means with a front side and a rear side, wherein the front side of the second diaphragm means is arranged so that it comes into direct contact with the patient's skin, and the rear side of the second diaphragm means is coupled to the first air cavity, where the second diaphragm means is arranged so that it does not come into direct physical contact with the first diaphragm means.

28. The stethoscope of claim 22 further including:

a second air cavity, coupled to the rear side of the first diaphragm means;

a second diaphragm means with a front side and a rear side, where the front side of the second diaphragm means is coupled to the second air cavity, and the rear side of the second diaphragm means is coupled to free air, wherein the first diaphragm means is arranged so that the air pressure applied to the rear side of the first diaphragm means is the pressure present within the second air cavity.

29. The stethoscope of claim 28 further including:

a third diaphragm means with a front side and a rear side, wherein the front side of the third diaphragm means is arranged so that it comes into direct contact with the patient's skin, and the rear side of the third diaphragm means is coupled to the first air cavity, where the third diaphragm means is arranged so that it does not come into direct physical contact with the first diaphragm means.

30. The stethoscope of claim 22 further including:

a second diaphragm means with a front side and a rear side, wherein the front side of the second diaphragm means is arranged so that it comes into direct contact with the patient's skin, and the rear side of the second diaphragm means is coupled to the first air cavity, where the second diaphragm means is arranged so that it does not come into direct physical contact with the first diaphragm means.

31. A stethoscope chestpiece for transducing skin vibrations with an increased signal to noise ratio, comprising:

a first air cavity adapted to be coupled to the skin;

a second air cavity;

a first diaphragm means with a front side and a rear side, where the front side of first diaphragm means is coupled to the second air cavity, and the rear side of first diaphragm means is coupled to free air; and transducer means coupled to the first and second air cavities, and not directly coupled to the patient's skin, wherein the transducer means outputs a signal in response to the pressure difference between the air pressure within the first air cavity and the air pressure within the second air cavity.

32. The stethoscope chestpiece of claim 31 in which the transducer means is comprised of a pressure gradient microphone.

33. The stethoscope chestpiece of claim 31 in which the transducer means includes second diaphragm means with a front side and a rear side, where the front side of the second diaphragm means is coupled to the first air cavity, and the rear side of the second diaphragm means is coupled to the second air cavity.

34. The stethoscope chestpiece of claim 33 in which the second diaphragm means has high mechanical impedance.

35. The stethoscope chestpiece of claim 33 further including means for converting the vibration of the second diaphragm means into an electrical signal.

36. The stethoscope chestpiece of claim 33 further including means for directly converting the vibration of the second diaphragm means into an acoustic pressure signal.

37. The stethoscope chestpiece of claim 36, in which the means for directly converting the vibration of the second diaphragm means into an acoustic pressure signal includes:

a third air cavity, coupled to the second diaphragm means, and a tube assembly, coupled to the third air cavity, for conducting the air pressure signal present in the third air cavity to the user's ears.

38. The stethoscope chestpiece of claim 36, in which the means for directly converting the vibration of the second diaphragm means into an acoustic pressure signal further includes:

a third air cavity coupled to one side of the second diaphragm means;

a fourth air cavity coupled to the other side of the second diaphragm means, in which the fourth air cavity is otherwise sealed from all other air cavities in the chestpiece assembly and from free air; and a tube assembly, coupled to the third air cavity, for conducting the air pressure signal present in the third air cavity to the user's ears.

39. The stethoscope chestpiece of claim 31 further including means for providing user adjustment of the acoustic compliance of the second air cavity.

40. The stethoscope chestpiece of claim 39 further including means for providing user adjustment of the acoustic mass of the air load applied to the side of the first diaphragm means that is coupled to free air.

41. The stethoscope chestpiece of claim 31 further including means for providing user adjustment of the acoustic mass of the air load applied to the side of the first diaphragm means that is coupled to free air.

42. The stethoscope chestpiece of claim 31 further including:

a noise sensor for detecting ambient noise proximate the transducer means, which outputs a noise signal;

filter means for filtering the noise signal; and means for subtracting the filtered noise signal from the transducer means output signal, to reduce the component due to ambient noise in the transducer means output signal.

43. The stethoscope of claim 31 further including:

a second diaphragm means with a front side and a rear side, wherein the front side of the second diaphragm means is arranged so that it comes into direct contact with the patient's skin, and the rear side of the second diaphragm means is coupled to the first air cavity.

\* \* \* \* \*